US012673080B1

(12) United States Patent
Ahmed Al-Jaziri et al.

(10) Patent No.: US 12,673,080 B1
(45) Date of Patent: Jul. 7, 2026

(54) COMPOSITIONS AND METHODS FOR TREATING HIV/AIDS

(71) Applicant: University of Jeddah, Jeddah (SA)

(72) Inventors: Maryam Ahmed Al-Jaziri, Jeddah (SA); Arwa A. Makki, Jeddah (SA); Dina Hajjar, Jeddah (SA)

(73) Assignee: University of Jeddah, Jeddah (SA)

( * ) Notice: Subject to any disclaimer, the term of this patent is extended or adjusted under 35 U.S.C. 154(b) by 0 days.

(21) Appl. No.: 19/224,624

(22) Filed: May 30, 2025

(51) Int. Cl.
  *A61K 36/482* (2006.01)
  *A61P 31/18* (2006.01)
(52) U.S. Cl.
  CPC ............ *A61K 36/482* (2013.01); *A61P 31/18* (2018.01); *A61K 2236/333* (2013.01); *A61K 2236/35* (2013.01); *A61K 2236/53* (2013.01)
(58) Field of Classification Search
  CPC ............ A61K 36/482; A61K 2236/333; A61K 2236/35; A61K 2236/53; A61P 31/18
  See application file for complete search history.

(56) References Cited

U.S. PATENT DOCUMENTS

| | | | |
|---|---|---|---|
| 5,827,896 | A | 10/1998 | Ostlund et al. |
| 8,192,767 | B2 * | 6/2012 | Carta ...................... A61P 29/00 424/725 |
| 11,642,389 | B2 * | 5/2023 | Prasad ................. A61K 9/0095 424/729 |
| 12,194,065 | B2 * | 1/2025 | Tripp ................... A61K 35/742 |
| 12,226,443 | B2 * | 2/2025 | Prasad ................. A61K 36/738 |
| 12,274,728 | B2 * | 4/2025 | Gomez ................. A23K 20/163 |
| 12,318,471 | B2 * | 6/2025 | Fousse ................. A61Q 19/08 |
| 12,527,832 | B2 * | 1/2026 | Antony ................. A61K 36/81 |

FOREIGN PATENT DOCUMENTS

WO          9924009 A1      5/1999

OTHER PUBLICATIONS

Thaker K, et al "Senna (Cassia angustifolia Vahl.): A comprehensive review of ethnopharmacology and phytochemistry" Pharmacological Res.—Natural Products, 1(100003), Dec. 2023 (ePub Nov. 22, 2023), 12 pages; doi: 10.1016/j.prenap.2023.100003. (Year: 2023).*
Zahoor M, et al "An ethnopharmacological evaluation of Navapind and Shahpur Virkanin district Sheikupura, Pakistan for their herbal medicines", J. Ethnobiol. Ethnomed, (2017) 13:27, 26 pages; DOI 10.1186/s13002-017-0151-1. (Year: 2017).*
Abd El-Hameed, et al., "Synthesis of Heterocyclic and Non-Heterocyclic Compounds Derived from Novel 2-Furanones and Evaluation of their Anti-Viral Activity", Journal of Advanced Pharmacy Research, vol. 5, No. 1, 2021, pp. 202-210.
Abdellatif, et al., "Review on Phytochemical Constituents of the Genus *Cassia*", Records of Pharmaceutical and Biomedical Sciences, vol. 7, No. 2, 2023, pp. 93-110.

Cheudjeu, Antony, "Correlation of D-xylose with Severity and Morbidity-Related Factors of COVID-19 and Possible Therapeutic use of D-xylose and Antibiotics for COVID-19", Life Science, vol. 260; 118335, 2020, 12 pages.
Cheudjeu, Antony, "D-Xylose, A Stimulator of Heparan Sulfate Biosynthesis, Exhibits Antiviral Properties Against SARS-CoV-2, ZIKV, HCMV and HIV-1 NL4-3 In Vitro", Research Square, 2023, pp. 1-28.
Debouck, Christine, "The HIV-1 Protease as a Therapeutic Target for AIDS", AIDS Research and Human Retroviruses, vol. 8, No. 2, 1992, pp. 153-164.
Dorababu, Atukuri, "Indole—A Promising Pharmacophore in recent Antiviral Drug Discovery", RSC Medicinal Chemistry, 2020, 19 pages.
Fouché, et al., "Wound Healing Effects of Aloe muth-muth: In Vitro Investigations Using Immortalized Human Keratinocytes (HaCaT)", Biology, vol. 9, Oct. 23, 2020, 10 pages.
Gonfa, et al., "Phytochemical Investigation and Potential Pharmacologically Active Compounds of Rumex nepalensis: An Appraisal", Beni-Suef University Journal of Basic and Applied Sciences, vol. 10, Mar. 18, 2021, 11 pages.
Hajjar, et al., "Anti-Cancer Agents in Saudi Arabian Herbals revealed by Automated High-Content Imaging", PLOS One, vol. 12, No. 6; e0177316, Jun. 13, 2017, 19 pages.
Laila, et al., "Role of Medicinal Plants in HIV/AIDS Therapy", Clinical and Experimental Pharmacology and Physiology, vol. 46, 2019, pp. 1063-1073.
Lee, et al., "Palmitic Acid is a Novel CD4 Fusion Inhibitor That Blocks HIV Entry and Infection", AIDS Research and Human Retroviruses, vol. 25, No. 12, 2009, pp. 1231-1241.
Leteane, et al., "Old Plants Newly Discovered: Cassia sieberiana D.C. and Cassia abbreviata Oliv. Oliv. Root Extracts Inhibit in Vitro HIV-1c Replication in Peripheral Blood Mononuclear Cells (PBMCs) by Different Modes of Action", Journal of Ethnopharmacology, vol. 141, 2012, pp. 48-56.
Monteiro, et al., "Molecular Docking of Fructose-Derived Nucleoside Analogs against Reverse Transcriptase of HIV-1", MOL2NET, International Conference on Multidisciplinary Sciences, 2019, 18 pages.
Omoruyi, et al., "Inhibition of HIV-1 Protease by *Carpobrotus edulis* (L.)", Evidence-Based Complementary and Alternative Medicine, vol. 2020; 9648056, Jun. 8, 2020, 14 pages.
Parvez, et al., "The Anti-Hepatitis B Virus Activity of Sea Buckthorn is Attributed to Quercetin, Kaempferol and Isorhamnetin", Biomedical Reports, vol. 17, 2022, 7 pages.

(Continued)

*Primary Examiner* — Aaron J Kosar
(74) *Attorney, Agent, or Firm* — Pabst Patent Group LLP

(57)          ABSTRACT

Compositions and methods for inhibiting HIV protease are disclosed. The compositions include an extract from *Cassia acutifolia* stems, or a fraction thereof, alone or in a pharmaceutically acceptable carrier. The extracts can be obtained by subjecting *Cassia acutifolia* pulverized stems to methanol/dichloromethane (1:1) extraction. In a first extraction stage, *Cassia acutifolia* pulverized stems are macerated in a mixture of methanol/dichloromethane. In a second stage methanol is added to the remaining marc vortex and extracted for a suitable time period at room temperature. The extract from the first and second stages are combined. The extracts can be further processed for formulation into a suitable pharmaceutical form.

20 Claims, 2 Drawing Sheets

(56)  References Cited

OTHER PUBLICATIONS

Popović-Djordjević, et al., "Natural Products and Synthetic Analogues against HIV: A Perspective to Develop New Potential Anti-HIV Drugs", European Journal of Medicinal Chemistry, vol. 233, 2022, 35 pages.

Sanna, et al., "Prenylated phloroglucinols from Hypericum scruglii, An Endemic Species of Sardinia (Italy), as New Dual HIV-1 Inhibitors Effective on HIV-1 Replication", PLoS One, vol. 13, No. 3; e0195168, Mar. 30, 2018, 19 pages.

Sillapachaiyaporn, et al., "Anti-HIV-1 Protease Activity of the Crude Extracts and Isolated Compounds from Auricularia polytricha", BMC Complementary and Alternative Medicine, vol. 19, 2019, 10 pages.

Wahedi, et al., "Aloesin from Aloe vera Accelerates Skin Wound Healing by Modulating MAPK/Rho and Smad Signaling Pathways in vitro and in vivo", Phytomedicine, vol. 28, 2017, pp. 19-26.

Wang, et al., "The Discovery of Indole-2-carboxylic Acid Derivatives as Novel HIV-1 Integrase Strand Transfer Inhibitors", Molecules, vol. 28, Dec. 8, 2023, 15 pages.

Yang, et al., "Arthproliferins A-D, Four New Sesterterpenes from the Mangrove-Sediment-Derived Fungus arthrinium sp. SCSIO41221", Molecules, vol. 28, Oct. 24, 2023, 11 pages.

Youssef, et al., "Synthesis and Antioxidant, Antimicrobial, and Antiviral Activity of some Pyrazole-Based Heterocycles using a 2(3H)-furanone Derivative", Journal of the Iranian Chemical Society, vol. 20, Jun. 3, 2023, pp. 2203-2216.

\* cited by examiner

COMPOSITIONS AND METHODS FOR TREATING HIV/AIDS

FIELD OF THE INVENTION

The invention is generally directed to compositions and methods of treating viral infections.

BACKGROUND OF THE INVENTION

According to the latest data from United Nations Program on HIV and AIDS (UNAIDS), 37.6 million individuals worldwide were infected with HIV in 2020, 1.5 million became subsequently infected with HIV, and 690,000 humans died of AIDS-related illnesses. Because of the limitations of antiretroviral (ART) treatments for human immunodeficiency virus (HIV) a drive remains for the continuous search for more efficient anti-HIV drugs.

It is challenging to suppress HIV-1 due to continuous viral replication in the first or during cumin phases. Therefore, many researchers tend to inhibit HIV viral proliferation in the last stages before their proteins form or are released and mature from the host. One of the crucial targets for pharmacological intervention in HIV infection is HIV-1 protease. Due to extensive structure-based medication design, protease is considered an excellent target for suppression of HIV in the last life stage, as it cleaves polyprotein precursors encoding the structural protein and enzymes of the virus. This proteolytic activity is required to produce mature, infectious virions and is, therefore, an attractive target for therapeutic intervention. This virus has caused the death of millions of people worldwide since the beginning of the pandemic (DEBOUCK, 1992) (Popović-Djordjević et al., 2022). Although treatments are available, they only temporarily relieve symptoms and do not eliminate the virus from the host. As a result, patients must live with this virus for their entire life. Because of the restricted availability of antiretroviral (ART) therapy for the treatment of AIDS, virus scientists have been continuously searching for more effective anti-HIV drugs. Medical studies have indicated that some medicinal herbs have significant antiviral potential, and some medicinal plants found to be highly functional against retroviruses may also have a remedial effect on HIV/AIDS (Laila et al., 2019).

There is a need to identify compounds and/or compositions containing compounds which can act as antivirals, and more importantly, which can suppress HIV replication and infection.

It is therefore an object of the present invention to provide composition with antiretroviral activity, which can be used suppress HIV replication and infections.

BRIEF SUMMARY OF THE INVENTION

Compositions and methods for inhibiting HIV protease are disclosed. The compositions include an extract from *Cassia acutifolia* stems, or a fraction thereof, alone or in a pharmaceutically acceptable carrier, preservative, and/or diluent. In some forms, the extracts is obtained by subjecting *Cassia acutifolia* pulverized stems to methanol/dichloromethane (1:1) extraction. Alternative solvents include polar solvents, such ethanol and dimethyl sulfoxide, preferably not including water. In a first extraction stage, *Cassia acutifolia* pulverized stems are macerated in a mixture of methanol/dichloromethane (1:1) overnight at room temperature (for about 12 hours). In a second stage 0.4 mL of methanol is added to the remaining marc vortex and extracted for a suitable time period (e.g., 30 mins) at room temperature. The extract from the first and second stages are combined. The extracts can be further processed for formulation into a suitable pharmaceutical form.

The disclosed data demonstrate that the extracts display antiretroviral activity by, for example, inhibiting HIV protease.

DETAILED DESCRIPTION OF THE INVENTION

Figure 1:
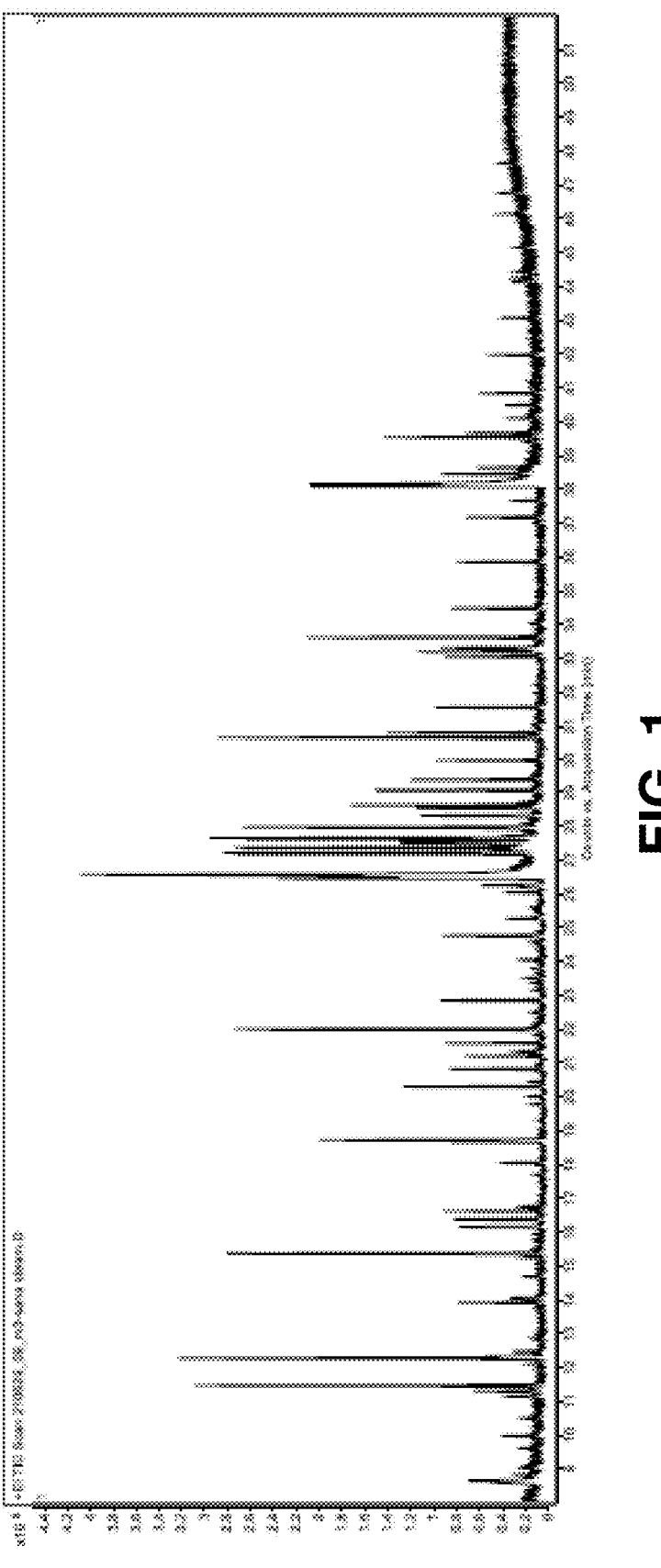
FIG. 1 is a GC-MS chromatogram of the primary components of *Cassia acutifolia* crude extract.

The disclosed compositions and methods are based on a study that extracted the primary and secondary constituents of plant segments (e.g., leaves and steams), and examined this crude extract for the first time against the HIV-1 virus by examining its inhibitory activity against HIV-1 protease. The data show effective inhibition of HIV-1 protease, pointing to effectiveness against the virion.

A. Definition

"Extract" refers to a substance derived from a source material through physical, chemical, or biological processes, where bioactive, functional, or structural components are isolated, concentrated, or modified for specific applications. The extract may exist in various forms, including but not limited to liquid, solid extract, lyophilized (freeze-dried) forms, crystalline compounds, semi-solid extract, encapsulated extract (entrapped within nanoparticles, microparticles, liposomes, or polymeric carriers for controlled release), fermented or biotransformed extract (modified via enzymatic, microbial, or chemical processes to enhance bioavailability or functionality). An extract may retain its original composition or be fractionated, purified, or reformulated for use in pharmaceutical applications.

"Aerosol" as used herein refers to any preparation of a fine mist of particles, which can be in solution or a suspension, whether or not it is produced using a propellant.

"Amphiphilic" as used herein refers to a molecule combining hydrophilic and lipophilic (hydrophobic) properties.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

A "cream" is a viscous liquid or semi-solid emulsion of either the "oil-in-water" or "water-in-oil type".

An "emulsion" is a composition containing a mixture of non-miscible components homogenously blended together.

"Gel" as used herein is a colloid in which the dispersed phase has combined with the continuous phase to produce a semisolid material, such as jelly.

"Hydrophilic" as used herein refers to substances that have strongly polar groups that readily interact with water.

"Hydrophobic" as used herein refers to substances that lack an affinity for water; tending to repel and not absorb water as well as not dissolve in or mix with water.

"Lipophilic" as used herein refers to compounds having an affinity for lipids.

A "lotion" is a low-to medium-viscosity liquid formulation.

"Oil" as used herein refers to a composition containing at least 95% wt of a lipophilic substance. Examples of lipophilic substances include but are not limited to naturally occurring and synthetic oils, fats, fatty acids, lecithins, triglycerides and combinations thereof.

An "ointment" is a semisolid preparation containing an ointment base and optionally one or more active agents.

"Parenteral administration", as used herein, means administration by any method other than through the digestive tract or non-invasive topical or regional routes.

"Patient" or "subject" to be treated as used herein refers to either a human or non-human animal.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Pharmaceutically acceptable salt", as used herein, refers to derivatives of the compounds defined herein, wherein the parent compound is modified by making acid or base salts thereof.

"Therapeutically effective" or "effective amount" as used herein means that the amount of the composition used is of sufficient quantity to ameliorate one or more causes or symptoms of a disease or disorder. Such amelioration only requires a reduction or alteration, not necessarily elimination. As used herein, the terms "therapeutically effective amount" "therapeutic amount" and "pharmaceutically effective amount" are synonymous. One of skill in the art can readily determine the proper therapeutic amount.

"Alkyl," as used herein, refers to the radical of saturated aliphatic groups, including straight-chain alkyl groups, branched-chain alkyl, and cycloalkyl (alicyclic). In some forms, a straight chain or branched chain alkyl has 30 or fewer carbon atoms in its backbone (e.g., $C_1$-$C_{30}$ for straight chains, $C_3$-$C_{30}$ for branched chains), 20 or fewer, 15 or fewer, or 10 or fewer. Alkyl includes methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Likewise, a cycloalkyl is a non-aromatic carbon-based ring composed of at least three carbon atoms, such as a nonaromatic monocyclic or nonaromatic polycyclic ring containing 3-30 carbon atoms, 3-20 carbon atoms, or 3-10 carbon atoms in their ring structure, and have 5, 6 or 7 carbons in the ring structure. Cycloalkyls containing a polycyclic ring system can have two or more non-aromatic rings in which two or more carbons are common to two adjoining rings (i.e., "fused cycloalkyl rings"). Examples of cycloalkyl groups include, but are not limited to, cyclopropyl, cyclobutyl, cyclopentyl, cyclohexyl, cycloheptyl, cyclooctanyl, etc.

"Substituted alkyl" refers to alkyl moieties having one or more substituents replacing a hydrogen on one or more carbons of the hydrocarbon backbone. Such substituents can be any substituents described above, e.g., halogen (such as fluorine, chlorine, bromine, or iodine), hydroxyl, carbonyl (such as a carboxyl, alkoxycarbonyl, formyl, or an acyl), thiocarbonyl (such as a thioester, a thioacetate, or a thioformate), aryl, alkoxyl, aralkyl, phosphonium, phosphanyl, phosphonyl, phosphoryl, phosphate, phosphonate, a phosphinate, amino, amido, amidine, imine, cyano, nitro, azido, oxo, sulfhydryl, thiol, alkylthio, silyl, sulfinyl, sulfate, sulfonate, sulfamoyl, sulfonamido, sulfonyl, heterocyclyl, an aromatic or heteroaromatic moiety. —NRR', wherein R and R' are independently hydrogen, alkyl, or aryl, and wherein the nitrogen atom is optionally quaternized; —SR, wherein R is a phosphonyl, a sulfinyl, a silyl a hydrogen, an alkyl, or an aryl; —CN; —NO$_2$; —COOH; carboxylate; —COR, —COOR, or —CON(R)$_2$, wherein R is hydrogen, alkyl, or aryl; imino, silyl, ether, haloalkyl (such as —CF$_3$, —CH$_2$—CF$_3$, —CCl$_3$); —CN; —NCOCOCH$_2$CH$_2$: —NCOCOCHCH; and —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, aralkyl, azido, imino, amido, phosphonium, phosphanyl, phosphoryl (including phosphonate and phosphinate), oxo, sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

"Heteroalkyl," as used herein, refers to straight or branched chain, or cyclic carbon-containing alkyl radicals, or combinations thereof, containing at least one heteroatom on the carbon backbone. Suitable heteroatoms include, but are not limited to, O, N, Si, P and S, wherein the nitrogen, phosphorous and sulfur atoms are optionally oxidized, and the nitrogen heteroatom is optionally quaternized. For example, the term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "alkenyl" as used herein is a hydrocarbon group of from 2 to 24 carbon atoms and structural formula containing at least one carbon-carbon double bond. Alkenyl groups include straight-chain alkenyl groups, branched-chain alkenyl, and cycloalkenyl. A cycloalkenyl is a non-aromatic carbon-based ring composed of at least three carbon atoms and at least one carbon-carbon double bond, such as a nonaromatic monocyclic or nonaromatic polycyclic ring containing 3-30 carbon atoms and at least one carbon-carbon double bond, 3-20 carbon atoms and at least one carbon-carbon double bond, or 3-10 carbon atoms and at least one carbon-carbon double bond in their ring structure, and have 5, 6 or 7 carbons and at least one carbon-carbon double bond in the ring structure. Cycloalkenyls containing a polycyclic ring system can have two or more non-aromatic rings in which two or more carbons are common to two adjoining rings (i.e., "fused cycloalkenyl rings") and contain at least one carbon-carbon double bond. Asymmetric structures such as (AB)C=C(C'D) are intended to include both the E and Z isomers. This may be presumed in structural formulae herein wherein an asymmetric alkene is present, or it may be explicitly indicated by the bond symbol C. The term "alkenyl" as used throughout the specification, examples, and claims is intended to include both "unsubstituted alkenyls" and "substituted alkenyls," the latter of which refers to alkenyl moieties having one or more substituents replacing a hydrogen on one or more carbons of the hydrocarbon backbone. The term "alkenyl" also includes "heteroalkenyl."

The term "substituted alkenyl" refers to alkenyl moieties having one or more substituents replacing one or more hydrogen atoms on one or more carbons of the hydrocarbon backbone. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, oxo, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

"Heteroalkenyl," as used herein, refers to straight or branched chain, or cyclic carbon-containing alkenyl radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. For example, the term "heterocycloalkenyl group" is a cycloalkenyl group where at least one of the carbon atoms of the ring is substituted with a heteroatom such as, but not limited to, nitrogen, oxygen, sulphur, or phosphorus.

The term "alkynyl group" as used herein is a hydrocarbon group of 2 to 24 carbon atoms and a structural formula containing at least one carbon-carbon triple bond. Alkynyl groups include straight-chain alkynyl groups, branched-chain alkynyl, and cycloalkynyl. A cycloalkynyl is a non-aromatic carbon-based ring composed of at least three carbon atoms and at least one carbon-carbon triple bond, such as a nonaromatic monocyclic or nonaromatic polycyclic ring containing 3-30 carbon atoms and at least one carbon-carbon triple bond, 3-20 carbon atoms and at least one carbon-carbon triple bond, or 3-10 carbon atoms and at least one carbon-carbon triple bond in their ring structure, and have 5, 6 or 7 carbons and at least one carbon-carbon triple bond in the ring structure. Cycloalkynyls containing a polycyclic ring system can have two or more non-aromatic rings in which two or more carbons are common to two adjoining rings (i.e., "fused cycloalkynyl rings") and contain at least one carbon-carbon triple bond. Asymmetric structures such as (AB)C=C(C"D) are intended to include both the E and Z isomers. This may be presumed in structural formulae herein wherein an asymmetric alkyne is present, or it may be explicitly indicated by the bond symbol C. The term "alkynyl" as used throughout the specification, examples, and claims is intended to include both "unsubstituted alkynyls" and "substituted alkynyls," the latter of which refers to alkynyl moieties having one or more substituents replacing a hydrogen on one or more carbons of the hydrocarbon backbone. The term "alkynyl" also includes "heteroalkynyl."

The term "substituted alkynyl" refers to alkynyl moieties having one or more substituents replacing one or more hydrogen atoms on one or more carbons of the hydrocarbon backbone. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, polyaryl, polyheteroaryl, and combinations thereof.

"Heteroalkynyl," as used herein, refers to straight or branched chain, or cyclic carbon-containing alkynyl radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. For example, the term "heterocycloalkynyl group" is a cycloalkynyl group where at least one of the carbon atoms of the ring is substituted with a heteroatom such as, but not limited to, nitrogen, oxygen, sulphur, or phosphorus.

"Aryl," as used herein, refers to $C_4$-$C_{26}$-membered aromatic rings or fused ring systems containing one aromatic ring and optionally one or more non-aromatic rings. Examples of aryl groups are benzene, tetralin, indane, etc.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocyclo" and "heterocyclyl" are used interchangeably, and refer to a cyclic radical attached via a ring carbon or nitrogen atom of a monocyclic ring or polycyclic ring system containing 3-30 ring atoms, 3-20 ring atoms, 3-10 ring atoms, or 5-6 ring atoms, where the polycyclic ring system contains one or more non-aromatic rings and optionally one or more aromatic rings, where at least one non-aromatic ring contains carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Heterocycles can be a heterocycloalkyl, a heterocycloalkenyl, a heterocycloalkynyl, etc., such as piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_3$-$C_{26}$-membered aromatic rings or fused ring systems containing one aromatic ring and optionally one or more non-aromatic rings, in which one or more carbon atoms on the aromatic ring structure have been substituted with a heteroatom. Suitable heteroatoms include, but are not limited to, oxygen, sulfur, and nitrogen. Examples of heteroaryl groups pyrrole, furan, thiophene, imidazole, oxazole, thiazole, triazole, tetrazole, pyrazole, pyridine, pyrazine, pyridazine and pyrimidine, and the like. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benziso-thiazolyl, benzimidazolinyl, carbazolyl, 4aH-carbazolyl, carbolinyl, chromanyl, chromenyl, cinnolinyl, decahydro-quinolinyl, 2H,6H-1,5,2-dithiazinyl, furanyl, furazanyl, imi-dazolidinyl, imidazolinyl, imidazolyl, 1H-indazolyl, indole-nyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methyl-enedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidi-nyl, phenanthridinyl, phenanthrolinyl, phenazinyl, phenothi-azinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothi-azolyl, thienooxazolyl, thienoimidazolyl, thiophenyl and xanthenyl. One or more of the rings can be substituted as defined below for "substituted heteroaryl."

The term "substituted heteroaryl" refers to a heteroaryl group in which one or more hydrogen atoms on one or more heteroaromatic rings are substituted with one or more sub-stituents including, but not limited to, halogen, azide, alkyl, aralkyl, alkenyl, alkynyl, cycloalkyl, hydroxyl, alkoxy, car-bonyl (such as a ketone, aldehyde, carboxyl, alkoxycarbo-nyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, $-CH_2-CF_3$, $-CCl_3$), —CN, aryl, heteroaryl, and combinations thereof.

The term "polyaryl" refers to a fused ring system that includes two or more aromatic rings and optionally one or more non-aromatic rings. Examples of polyaryl groups are naphthalene, anthracene, phenanthrene, chrysene, pyrene, corannulene, coronene, etc. When a fused ring system containing two or more aromatic rings and optionally one or more non-aromatic rings, in which one or more carbon atoms on two or more aromatic ring structures have been substituted with a heteroatom, the fused ring system can be referred to as a "polyheteroaryl". When a fused ring system containing two or more aromatic rings and optionally one or more non-aromatic rings, in which one or more carbon atoms in the fused ring system is substituted with a heteroa-tom it can be referred to as a "heteropolyaryl." The term "substituted polyaryl" refers to a polyaryl in which one or more of the aryls are substituted, with one or more substitu-ents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thio-acetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfona-mido, sulfonyl, heterocyclyl, alkylaryl, haloalkyl, —CN, aryl, heteroaryl, and combinations thereof. When a polyhet-eroaryl is involved, the chemical moiety can be referred to as a "substituted polyheteroaryl."

The term "cyclic ring" or "cyclic group" refers to a substituted or unsubstituted monocyclic ring or a substituted or unsubstituted polycyclic ring (such as those formed from single or fused ring systems), such as a substituted or unsubstituted cycloalkyl, a substituted or unsubstituted cycloalkenyl, a substituted or unsubstituted cycloalkynyl, or a substituted or unsubstituted heterocyclyl, that have from three to 30 carbon atoms, as geometric constraints permit. The substituted cycloalkyls, cycloalkenyls, cycloalkynyls, and heterocyclyls are substituted as defined above for the alkyls, alkenyls, alkynyls, and heterocyclyls, respectively.

The term "aralkyl" as used herein is an aryl group or a heteroaryl group having an alkyl, alkynyl, or alkenyl group as defined above attached to the aromatic group, such as an aryl, a heteroaryl, a polyaryl, or a polyheteroaryl. An example of an aralkyl group is a benzyl group.

The terms "alkoxyl" or "alkoxy," "aroxy" or "aryloxy," generally describe compounds represented by the formula $-OR^v$, wherein $R^v$ includes, but is not limited to, a substi-tuted or unsubstituted alkyl, a substituted or unsubstituted alkenyl, a substituted or unsubstituted alkynyl, a substituted or unsubstituted cycloalkyl, a substituted or unsubstituted heterocyclyl, a substituted or unsubstituted cycloalkenyl, a substituted or unsubstituted heterocycloalkenyl, a substi-tuted or unsubstituted aryl, a substituted or unsubstituted heteroaryl, a substituted or unsubstituted polyaryl, a substi-tuted or unsubstituted polyheteroaryl, a substituted or unsub-stituted arylalkyl, a substituted or unsubstituted heteroalkyl, a substituted or unsubstituted alkylaryl, a substituted or unsubstituted alkylheteroaryl, a substituted or unsubstituted aralkyl, a substituted or unsubstituted carbonyl, a phospho-nium, a phosphanyl, a phosphonyl, a sulfinyl, a silyl, a thiol, an amido, and an amino. Exemplary alkoxyl groups include methoxy, ethoxy, propyloxy, tert-butoxy and the like. A "lower alkoxy" group is an alkoxy group containing from one to six carbon atoms. An "ether" is two functional groups covalently linked by an oxygen as defined below. Accord-ingly, the substituent of an alkyl that renders that alkyl an ether is or resembles an alkoxyl, such as can be represented by one of —O-alkyl, —O-alkenyl, —O-alkynyl, —O-ara-kyl, —O-aryl, —O-heteroaryl, —O-polyaryl, —O-polyhet-eroaryl, —O-heterocyclyl, etc.

The term "substituted alkoxy" refers to an alkoxy group having one or more substituents replacing one or more hydrogen atoms on one or more carbons of the alkoxy backbone. Such substituents can be any substituents described above, e.g., halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thio-carbonyl (such as a thioester, a thioacetate, or a thioformate), alkoxyl, phosphonium, phosphanyl, phosphoryl, phosphate, phosphonate, phosphinate, amino (e.g. quarternized amino), amido, amidine, imine, cyano, nitro, azido, sulfhydryl, alkylthio, oxo, sulfate, sulfonate, sulfamoyl, sulfonamido, sulfonyl, heterocyclyl, alkylaryl, haloalkyl, —CN, aryl, het-eroaryl, and combinations thereof.

The term "heteroatom" as used herein means an atom of any element other than carbon or hydrogen. Preferred het-eroatoms are boron, nitrogen, oxygen, phosphorus, sulfur, and selenium. Other heteroatoms include silicon and arsenic.

As used herein, the term "nitro" means $-NO_2$; the term "halogen" designates —F, —Cl, —Br, or —I; the term "sulfhydryl" means —SH; the term "hydroxyl" means —OH; and the term "sulfonyl" means —SO2-.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include a substituted or unsubstituted alkyl, a substituted or unsubstituted alkenyl, a substituted or unsubstituted alkynyl, a substituted or unsubstituted heterocyclyl, a substituted or unsubstituted phenyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a halogen, a hydroxyl, an alkoxy, a phenoxy, an aroxy, a silyl, a thiol, an alkylthio, a substituted alkylthio, a phenylthio, an arylthio, a cyano, an isocyano, a nitro, a substituted or unsubstituted carbonyl, a carboxyl, an amino, an amido, an oxo, a sulfinyl, a sulfonyl, a sulfonic acid, a phosphonium, a phosphanyl, a phosphoryl, a phosphonyl, an amino acid. Such a substituted or unsubstituted alkyl, a substituted or unsubstituted alkenyl, a substituted or unsubstituted alkynyl, a substituted or unsubstituted heterocyclyl, a substituted or unsubstituted phenyl, a substituted or unsubstituted aryl, a substituted or unsubstituted heteroaryl, a substituted or unsubstituted polyaryl, a substituted or unsubstituted polyheteroaryl, a substituted or unsubstituted aralkyl, a halogen, a hydroxyl, an alkoxy, a phenoxy, an aroxy, a silyl, a thiol, an alkylthio, a substituted alkylthio, a phenylthio, an arylthio, a cyano, an isocyano, a nitro, a substituted or unsubstituted carbonyl, a carboxyl, an amino, an amido, an oxo, a sulfinyl, a sulfonyl, a sulfonic acid, a phosphonium, a phosphanyl, a phosphoryl, a phosphonyl, and an amino acid can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

B. Composition

1. Extract and Extraction Solvent Systems

Compositions and methods, preferably for inhibiting HIV protease are described. In some forms, the compositions include an extract from a non-leaf portion of *Cassia acutifolia*, preferably *Cassia acutifolia* stems, and a solvent/ combination of solvents. The solvent used for the extraction of medicinal plants is also known as the menstruum. In general, extraction procedures include maceration, digestion, decoction, infusion, percolation, Soxhlet extraction, superficial extraction, ultrasound-assisted, and/or microwave-assisted extractions. Fractionation and purification of phytochemical substances can be achieved through application of various chromatographic techniques such as paper chromatography, thin-layer chromatography, gas chromatography, and/or high-performance liquid chromatography.

In some forms, the disclosed compositions contain an extract of *Cassia acutifolia* and an organic solvent or mixture or organic solvents containing a non-naturally occurring organic solvent. Preferably, the extract is obtained from a non-leaf portion of *Cassia acutifolia*. In more preferred forms, the non-leaf portion of *Cassia acutifolia* is a stem portion. The non-naturally occurring organic solvent can be water-miscible, non-water-miscible, and/or volatile. Examples of non-naturally occurring organic solvents suitable for inclusion in the disclose formulations include, but are not limited to, dichloromethane, dimethyl sulfoxide, propylene glycol, poly(ethylene glycol), ethyl acetate, benzyl alcohol, glycerol, ethanol, dimethyl formamide, acetone, etc. In some forms, the organic solvent or mixture containing a non-naturally occurring organic solvent can be in residual amounts as required by the United States Food and Drug Administration. In some forms, the disclosed compositions contain an extract that includes one or more solvents of phytochemicals, including primary and secondary metabolites from *Cassia acutifolia* as disclosed in table 1 and table 2. In some forms, the composition contains an extract and one or more non-naturally occurring organic solvents such as dichloromethane or DMSO and demonstrate antiviral activity. In some forms, the composition also contains methanol and one or more of these non-naturally occurring organic solvents, and preferably display antiviral activity.

In some forms, the extract from *Cassia acutifolia* stems is obtained by subjecting *Cassia acutifolia* pulverized stems to methanol/dichloromethane (1:1) extraction (e.g., methanol/dicholoromethane (1:1) extraction). The selection of a solvent is determined by its efficacy in dissolving a wide range of active organic compounds, which depends on solid-liquid extraction. Alternative extraction solvents mixture can be used instead of those utilized here, for example. (ethanol: water, methanol: ethyl acetate, ethanol: ethyl acetate, methanol: water, dichloromethane: ethanol). In a first extraction stage, *Cassia acutifolia* pulverized stems are macerated in a mixture of 1.5 mL methanol/dichloromethane (1:1) overnight at room temperature (for about 12 hours). Maceration is an extraction procedure in which coarsely powdered drug material, either leaves or stem bark or root bark, is placed inside a container; the menstruum is poured on top until it completely covers the drug material and kept for an effective amount of time for the extraction to occur. In some forms, the time is at least 12 hours, and it can be up to 3 days, for example, 14, 16, 18, 20, 24, 26, 28, 30, 32, 34 and 36 hrs.

In a second stage a suitable volume (e.g., 0.4 mL) of an alcohol (e.g., methanol) can be added to the remaining marc vortex and extracted for a suitable time (e.g., 30 min) at room temperature. In maceration, "marc" refers to the solid, leftover plant material that remains after the desired compounds have been extracted from it by soaking in a solvent.

The extract from the first and second stages can be combined. Preferably, the extracts can be further processed for formulation into a suitable pharmaceutical form.

In some forms, the disclosed compositions demonstrate antiretroviral activity against HIV.

*Cassia* is a genus of flowering plants in the family Leguminaceae/Fabaceae that includes about 500 species distributed worldwide.

2. Pharmaceutically Acceptable Salts

In some forms, the disclosed compositions can also include one or more compounds in one or more of the compounds' pharmaceutically acceptable salts. Examples of pharmaceutically acceptable salts include, but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, MD, 2000, p. 704; and "Handbook of Pharmaceutical Salts: Properties, Selection, and Use," P. Heinrich Stahl and Camille G. Wermuth, Eds., Wiley-VCH, Weinheim, 2002.

3. Formulations

The compositions described herein can be formulated for enteral, parenteral, topical, or pulmonary administration. The compositions can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

In some forms, the extract itself has a physical or chemical property that is different from the physical or chemical property of the extract formulated in a formulation or composition together with a suitable excipient at an effective amount. For example, the extract by itself can be a colorless oil or liquid prior to being formulated in a pharmaceutical formulation; the extract transforms into a different physical form, such as a solution, suspension, or a powder, after being formulated with an effective amount of excipient in the pharmaceutical formulation. For example, the extract by itself is stable for up to a month; after being formulated with a suitable excipient at an effective amount in a pharmaceutical formulation, the extract is stable for at least three months, at least 6 months, at least 1 year, at least 1.5 years, at least 2 years, up to 5 years, or up to 10 years.

i. Parenteral Formulations

The compositions described herein can be formulated for parenteral administration. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the extracts or one or more compounds in the extract as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

| Preservative concentrations recommended for parental preparation | |
| --- | --- |
| Benzyl Alcohol | 0.5 to 10% |
| Benzalkonium Chloride | 0.01% |
| Butyl Paraben | 0.015% |
| Chlorobutanol | 0.25 to 0.5% |
| Meta Cresol | 01 to 0.25% |
| Chlorocresol | 0.1 to 0.18% |
| Methyl Paraben | 0.01 to 0.5% |
| Phenyl Ethyl Alcohol | 0.25 to 0.002% |
| Propyl Paraben | 0.005 to 0.002% |
| Phenol | 0.065 to 0.02% |
| Preservative Concentration for Liquid Oral Preparation | |
| Benzonic Acid | 0.1 to 0.2% |
| Sorbic Acid | 0.1 to 0.2% |
| Methyl Paraben | 0.25% |
| Propyl Paraben | 0.5 to 0.25% |

13

-continued

| | |
|---|---|
| Sodium Benzonate | 0.1 to 0.2% |
| Bronidol | 0.001 to 0.05% |
| Propylene Glycol | 0.25% |

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

a. Controlled Release Formulations

The parenteral formulations described herein can be formulated for controlled release including immediate release, delayed release, extended-release, pulsatile release, and combinations thereof.

(A) Nanoparticles and Microparticles

For parenteral administration, the extract and compounds therein, and optionally one or more additional active agents, can be incorporated into microparticles, nanoparticles, or combinations thereof that provide controlled release of the extract, compounds therein, and/or one or more additional active agents. In embodiments wherein the formulations contain two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.)

For example, the extract, compounds therein, and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

(B) Method of Making Nanoparticles and Microparticles Containing an Extract and Compounds Therein Encapsulation or incorporation of the extract and compounds therein into carrier materials to produce extract-containing nanoparticles or microparticles can be achieved through known pharmaceutical formulation techniques. In the case of formulation in fats, waxes or wax-like materials, the carrier material is typically heated above its melting temperature and the extract is added to form a mixture extract suspended in the carrier material, extract dissolved in the carrier material, or a mixture thereof. Microparticles and nanoparticles can be subsequently formulated through several methods including, but not limited to, the processes of congealing, extrusion, spray chilling or aqueous dispersion. In some forms, wax is heated above its melting temperature, extract is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce extract-containing nanoparticles or microparticles. In this case extract and carrier material are co-dissolved in a mutual solvent and nanoparticles or microparticles can subsequently be produced by several techniques including, but not limited to, forming an emulsion in water or other appropriate media, spray drying or by evaporating off the solvent from the bulk solution and milling the resulting material.

In some embodiments, extract in a particulate form is homogeneously dispersed in a water-insoluble or slowly water-soluble material. To minimize the size of the extract particles within the composition, the extract powder itself may be milled to generate fine particles prior to formulation. The process of jet milling, known in the pharmaceutical art, can be used for this purpose. In some embodiments extract in a particulate form is homogeneously dispersed in a wax or wax-like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto nanoparticles/microparticles or extract particles. Zein is an example of a naturally water-insoluble protein. It can be coated onto extract containing nanoparticles/microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing nanoparticles, microparticles or extract particles, a water-soluble protein can be spray coated onto the nanoparticles or microparticles and subsequently cross-linked by the one of the methods described above. Alternatively, extract-containing nanoparticles or microparticles can be encapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

ii. Injectable/Implantable Formulations

The compositions described herein can be incorporated into injectable/implantable solid or semi-solid implants, such as polymeric implants. In one embodiment, the compositions are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compositions can be incorporated into a polymer matrix and molded, compressed, or extruded into a device that is a solid at room temperature. For example, the compositions can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the extract or one or more compounds therein from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

iii. Enteral Formulations

Suitable oral dosage forms include tablets, chews, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof. Carrier also includes all components of the coating composition, which may include plasticizers, pigments, colorants, stabilizing agents, and glidants.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

a. Controlled Release Enteral Formulations

Oral dosage forms, such as capsules, tablets, solutions, and suspensions, can for formulated for controlled release. For example, the extract and optionally one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the extract and a controlled release polymer or matrix. Alternatively, the extract particles can be coated with one or more controlled release coatings prior to incorporation into the finished dosage form.

In another embodiment, the extract and optionally one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended-release coatings. The coating or coatings may also contain the compounds and/or additional active agents.

(A) Extended-Release Dosage Forms

The extended-release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof. In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename EUDRAGIT®. In further preferred embodiments, the acrylic polymer contains a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multi-particulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT t® RS, and 10% EUDRAGIT® RL and 90% EUDRAGIT® RS. One skilled in the art will recognize that other acrylic polymers may also be used, such as, for example, EUDRAGIT® L.

Alternatively, extended-release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended-release system by means of either applying an immediate release layer on top of the extended-release core using a coating or compression process or in a multiple unit system such as a capsule containing extended and immediate release beads.

Extended-release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils. Extended-release tablets containing wax materials are generally prepared using methods known in the art such as a direct blend method, a congealing method, and an aqueous dispersion method. In the congealing method, the drug is mixed with a wax material and either spray-congealed or congealed and screened and processed.

(B) Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating an extract or a extract-containing composition with a selected coating material. The extract-containing composition may be, e.g., a tablet for incorporation into a capsule, a tablet for use as an inner core in a "coated core" dosage form, or a plurality of extract-containing beads, particles or granules, for incorporation into either a tablet or capsule. Preferred coating materials include bio-erodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

iv. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The extract can also be formulated for intranasal delivery, pulmonary delivery, or inhalation. The compositions may further contain one or more chemical penetration enhancers, membrane permeability agents, membrane transport agents, emollients, surfactants, stabilizers, buffers, and combination thereof.

In certain embodiments, it may be desirable to provide continuous delivery of one or more compounds to a patient in need thereof. For topical applications, repeated application can be done or a patch can be used to provide continuous administration of the compounds over an extended period of time.

"Buffers" are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

"Emollients" are an externally applied agent that softens or soothes skin and are generally known in the art and listed in compendia, such as the "Handbook of Pharmaceutical Excipients", 4th Ed., Pharmaceutical Press, 2003. These include, without limitation, almond oil, castor oil, *ceratonia* extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

"Penetration enhancers" are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

"Preservatives" can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

a. Emulsions

An emulsion is a preparation of one liquid distributed in small globules throughout the body of a second liquid. In particular embodiments, the non-miscible components of the emulsion include a lipophilic component and an aqueous component. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

b. Lotions

A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

c. Creams

Creams may contain emulsifying agents and/or other stabilizing agents. In one embodiment, the formulation is in the form of a cream having a viscosity of greater than 1000 centistokes, typically in the range of 20,000-50,000 centistokes. Creams are often preferred over ointments, as they are generally easier to spread and easier to remove. The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

d. Ointments

Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

e. Gels

Gels are semisolid systems containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

f. Foams

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases, which can produce flammable or explosive vapors during spraying. Furthermore, the compositions preferably contain no volatile alcohols, which can produce flammable or explosive vapors during use.

v. Pulmonary Formulations

In one embodiment, the compositions are formulated for pulmonary delivery, such as intranasal administration or oral inhalation.

The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions including low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the sub epithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per cm3, porous endothelial basement membrane, and it is easily accessible.

Carriers for pulmonary formulations can be divided into those for dry powder formulations and for administration as solutions. Aerosols for the delivery of therapeutic agents to the respiratory tract are known in the art. Aerosols can be produced using standard techniques, such as ultrasonication or high-pressure treatment. For administration via the upper respiratory tract, the formulation can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxy-benzoate.

Solvents that are low toxicity organic (i.e. nonaqueous) class 3 residual solvents, such as ethanol, acetone, ethyl acetate, tetrahydofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, CA).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

C. Methods of Using

1. Methods of Treating

Methods of treatment can include methods of preventing viral infection and methods of treating viral infections. Provided herein is a method for treating a viral infection in a subject, involving administering to the subject therapeutically effective amount of a composition as described herein. The subject may or may not be infected with the target virus at the time of administrating to the subject. It will be appreciated that the disclosed methods can be methods of treatment of the symptoms and conditions described herein. "Treatment" refers to the medical management of a patient with the intent to cure, ameliorate, or stabilize, a disease, pathological condition, or disorder, such as HIV/AIDS. This term includes active treatment, that is, treatment directed specifically toward the improvement of a disease, pathological condition, or disorder, such as HIV/AIDS and also includes causal treatment, that is, treatment directed toward removal of the cause of the associated disease, pathological condition, or disorder, such as HIV/AIDS. In addition, this term includes palliative treatment, that is, treatment designed for the relief of symptoms rather than the curing of the disease, pathological condition, or disorder, such as HIV/AIDS; preventative treatment, that is, treatment directed to minimizing or partially or completely inhibiting the development of the associated disease, pathological condition, or disorder, such as HIV/AIDS; and supportive treatment, that is, treatment employed to supplement another specific therapy directed toward the improvement of the associated disease, pathological condition, or disorder, such as HIV/AIDS.

Any of the methods can include administering an effective amount of a disclosed formulation to the subject. An effective amount or therapeutically effective amount means a dosage and/or other element (e.g., amount of time) sufficient to treat, inhibit, or alleviate one or more symptoms of a disease state being treated, such as HIV/AIDS, or to otherwise provide a desired pharmacologic and/or physiologic effect. The precise dosage will vary according to a variety of factors such as subject-dependent variables (e.g., age, immune system health, etc.), the disease, and the treatment being administered.

i. Infections

The disclosed compositions and combinations thereof can be administered as described above in an amount effective to inhibit infections in a subject, preferably a human subject. The compositions and combinations thereof inhibit growth and/or reproduction of the microbe and thereby helps reduce or inhibit the infection. The infection can be systemic or local.

In certain embodiments, it may be desirable to provide continuous delivery of one or more compounds to a patient in need thereof. For intravenous or intraarterial routes, this can be accomplished using drip systems, such as by intravenous administration. For topical applications, repeated application can be done or a patch can be used to provide continuous administration of the compounds over an extended period of time.

ii. Viral Infections

The disclosed compositions and combinations thereof can be administered as described above in an amount effective to inhibit viral infections.

In some forms, the disclosed compositions combinations thereof can be administered as described above in an amount effective to inhibit retroviral infections such as but not limited to Human T-lymphotropic virus (HTLV-1, HTLV-2), Human immunodeficiency virus (HIV-1, HIV-2), Simian immunodeficiency virus (SIV), Feline immunodeficiency virus (FIV), Equine infectious anemia virus (EIAV), Avian leukosis virus (ALV), Rous sarcoma virus (RSV), Human foamy virus (HFV), Simian foamy virus (SFV), Mouse mammary tumor virus (MMTV), Jaagsiekte sheep retrovirus (JSRV), Murine leukemia virus (MLV), Human endogenous retroviruses (HERVs), or a combination thereof.

In some forms, the disclosed compositions and combinations thereof demonstrate antiretroviral activity against HIV-1 protease.

In some forms, the disclosed compositions and combinations thereof can be administered as described above in an amount effective to inhibit viruses in categories such as but not limited to respiratory viruses, enteric viruses, hepatotropic viruses, neurotropic viruses, sexually transmitted viruses, arboviruses, oncogenic viruses, hemorrhagic fever viruses, skin and mucosal viruses or zoonotic viruses.

iii. Combination Therapies

The disclosed compositions can be administered with a second therapeutic, including but not limited to one or more anti-fungal agents, antibacterial agents, anti-cancer agents, and combinations thereof.

a. Anti-Viral Agents

A variety of known anti-viral agents can be used to prepare the described compositions. Suitable antivirals include, without limitation, Acyclovir, Valacyclovir, Famciclovir, Penciclovir, Ganciclovir, Valganciclovir, Foscarnet, Cidofovir, Oseltamivir, Zanamivir, Peramivir, Baloxavir, Sofosbuvir, Ledipasvir, Velpatasvir, Glecaprevir, Pibrentasvir, Daclatasvir, Ribavirin, Tenofovir, Emtricitabine, Zidovudine, Abacavir, Lamivudine, Efavirenz, Etravirine, Nevirapine, Rilpivirine, Ritonavir, Atazanavir, Darunavir, Lopinavir, Raltegravir, Dolutegravir, Bictegravir, Maraviroc, Enfuvirtide, Remdesivir, Favipiravir, Molnupiravir, Nirmatrelvir/Ritonavir, Palivizumab, Interferon-alpha, Pegylated interferon-alpha.

b. Anti-Fungal Agents

A variety of known antifungal agents can be used to prepare the described compositions. A list of potential antifungal agents can be found in "Martindale—The Complete Drug Reference", 32nd Ed., Kathleen Parfitt, (1999) on pages 367-389. Suitable antifungals include, without limitation, amphotericin, amorolfine, bifonazole, bromochlorosalicyanilide, buclosamide, butenafine, butoconazole, candicidin, chlordantoin, chlormidazole, chlorphenesin, chlorxylenol, ciclopirox olamine, cilofungin, clotrimazole, croconazole, eberconazole, econazole, enilconazole, fenticlor, fenticonazole, fluconazole, flucytosine, griscofulvin, hachimycin,haloprogin, hydroxystilbamine, isethionate, iodochlorohydroxyquinone, isoconazole, itraconazole, ketoconazole, lanoconazole, luflucarban, mepartricin, miconazole, naftifine, natamycin, neticonazole, nifuroxime, nystatin, omoconazole, oxiconazole, pentamycin, propionic acid, protiofate, pyrrolnitrin, ravuconazole, saperconazole, selenium sulfide, sertaconazole, sulbentine, sulconazole, terbinafine, terconazole, tioconazole, tolciclate, tolnaftate, triacetin, timidazole, undecenoic acid, voriconazole and combinations thereof. Some of these agents are known to have antibacterial activity as well.

In one embodiment, the anti-fungal agent(s) is an azole. Suitable imidazole and triazole antifungal agents are fluconazole, timidazole, secnidazole, miconazole nitrate, econazole, haloprogin, metronidazole, itraconazole, terconazole, posaconazole, ravuconazole, ketoconazole, clotimazole, sapirconazole and combinations thereof.

In an alternative embodiment, the anti-fungal agent(s) is chlorxylenol, undecyclenic acid, selenium sulfide, iodochlorohydroxyquinone, bromochlorosalicyanilide, triacetin or combinations thereof.

Other antifungal agents include bensuldazic acid, benzoic acid, biphenamine, cloconazole, cloxyquin, dermostatin, halethazole, monensin, oxiconazole, nitrate, pecilocin, pyrithione, rubijervine, terbinafine, ticonazole, and undecylinic acid.

c. Antibacterial Agents

A variety of known antibacterial agents can be used to prepare the described compositions. A list of potential antibacterial agents can be found in "Martindale—The Complete Drug Reference", 32nd Ed., Kathleen Parfitt, (1999) on pages 112-270. Classes of useful antibacterials include aminoglycosides, antimycobacterials, cephalosporins and betalactams, chloramphenicols, glycopeptides, lincosamides, macrolides, penicillins, quinolones, sulphonamides and diaminopyridines, tetracyclines, and miscellaneous. In a preferred embodiment, the antibacterial agent is selected from the group consisting of metronidazole, timidazole, secnidazole, erythromycin, bactoban, mupirocin, neomycin, bacitracin, cicloprox, fluoriquinolones, ofloxacin, cephalexin, dicloxacillin, minocycline, rifampin, famciclovir, clindamycin, tetracycline and gentamycin.

Suitable aminoglycosides include antibiotics derived from *Streptomyces* and other actinomycetales, including streptomycin, framycetin, kanamycin, neomycin, paramomycin, and tobramycin, as well as gentamycin, sissomycin, netilmycin, isepamicin, and micronomycin.

Suitable antimycobacterials include rifamycin, rifaximin, rifampicin, rifabutinisoniazid, pyrazinamide, ethambutol, streptomycin, thiacetazone, aminosalicylic acid, capreomycin, cycloserine, dapsone, clofazimine, ethionamide, prothionamide, ofloxacin, and minocycline.

Cephalosporins and beta-lactams generally have activity against gram-positive bacteria and newer generations of compounds have activity against gram-negative bacteria as well. Suitable cephalosporins and beta-lactams include:

First generation; cephalothin, cephazolin, cephradine, cephaloridine, cefroxadine, cephadroxil, cefatrizine, cephalexin, pivcephalexin, cefaclor, and cefprozil.

Second generation; cephamandole, cefuroxime axetil, cefonicid, ceforanide, cefotiam, and cephamycin.

Third generation; cefotaxime, cefmenoxime, cefodizime, ceftizoxime, ceftriaxone, cefixime, cefdinir, cefetamet, cefpodoxime, ceftibuten, latamoxef, ceftazidime, cefoperazone, cefpiramide, and cefsulodin.

Fourth generation: cefepime and cefpirome

Other cephalosporins include cefoxitim, cefmetazole, cefotetan, cefbuperazone, cefminox, imipenem, meropenem, aztreonam, carumonam, and loracarbef.

Chloramphenicols inhibit gram positive and gram-negative bacteria. Suitable cloramphenicols include chloramphenicol, its sodium succinate derivative, thiamphenicol, and azidamfenicol.

Suitable glycopeptides include vancomycin, teicoplanin, and ramoplanin. Suitable lincosamides include lincomycin and clindamycin, which are used to treat primarily aerobic infections.

Macrolides have a lactam ring to which sugars are attached. Suitable macrolides include erythromycin, as well as spiromycin, oleandomycin, josamycin, kitamycin, midecamycin, rokitamycin, azithromycin, clarithromycin, dirithromycin, roxithromycin, flurithromycin, tylosin; and streptgramins (or synergistins) including pristinamycin, and virginiamycin; and combinations thereof.

Suitable penicillins include natural penicillin and the semisynthetic penicillins F, G, X, K, and V. Newer penicillins include phenethicillin, propicillin, methicillin, cloxacillin, dicloxacillin, flucloxacillin, oxacillin, nafcillin, ampicillin, amoxicillin, bacampicillin, hetacillin, metampicillin, pivampicillin, carbenecillin, carfecillin, carindacillin, sulbenecillin, ticarcillin, azlocillin, mezlocillin, piperacillin, temocillin, mecillinam, and pivemecillinam. Lactamase inhibitors such as clavulanic acid, sulbactam, and tazobacytam are often co-administered.

Suitable quinolones include nalidixic acid, oxolinic acid, cinoxacin, acrosoxacin, pipemedic acid, and the fluoroquinolones flumequine, ciprofloxacin, enoxacin, fleroxacin, grepafloxacin, levofloxacin, lomefloxacin, nadifloxacin, norfloxacin, ofloxacin, pefloxacin, rufloxacin, sparfloxacin, trovafloxacin, danofloxacin, enrofloxacin, and marbofloxacin.

Sulphonamides and diaminopyridines include the original of the "sulfa" drugs, sulphanilamide, and a large number of derivatives, including sulfapyridine, sulfadiazine, sulfafurazole, sulfamethoxazole, sulfadimethoxine, sulfadimethoxydiazine, sulfadoxine, sulfametopyrazine, silver sulfadiazine, mafenide acetate, and sulfasalizine, as well as related compounds including trimethoprim, baquiloprim, brodimoprim, ormetoprim, tetroxoprim, and in combinations with other drugs such as co-trimoxazole.

Tetracyclines are typically broad-spectrum and include the natural products chlortetracycline, oxytetracycline, tetracycline, demeclocycline, and semisynthetic methacycline, doxycycline, and minocycline.

Suitable antibacterial agents that do not fit into one of the categories above include spectinomycin, mupirocin, newmycin, fosfomycin, fusidic acid, polymixins, colistin, bacitracin, gramicidin, tyrothricin, clioquinol, chloroquinaldol, haloquinal, nitrofurantonin, nitroimidazoles (including metronizole, timidazole and secnidazole), and hexamine.

The antibiotic and antifungal agents may be present as the free acid or free base, a pharmaceutically acceptable salt, or as a labile conjugate with an ester or other readily hydrolysable group, which are suitable for complexing with the ion-exchange resin to produce the resinate.

vi. Methods of Administration and Dosage Regimes

The combination therapies and treatment regimens typically include treatment of a disease or symptom thereof, or a method for achieving a desired physiological change, including administering to an animal, such as a mammal, especially a human being, an effective amount of the disclosed compounds to treat the disease or symptom thereof, or to produce the physiological change, wherein the chemical agents or components are administered together, such as part of the same composition, or administered separately and independently at the same time or at different times (i.e., administration of niacin and tranexamic acid is separated by a finite period of time from each other). Therefore, the term "combination" or "combined" is used to refer to either concomitant, simultaneous, or sequential administration of the niacin and tranexamic acid. The combinations can be administered either concomitantly (e.g., as an admixture), separately but simultaneously (e.g., via separate intravenous lines into the same subject; one agent is given orally while the other agent is given by infusion or injection, etc.,), or sequentially (e.g., one agent is given first followed by the second).

In some forms, administration of the composition achieves a result greater than when administered alone or in isolation. For example, in some embodiments, the result achieved by the combination is partially or completely additive of the results achieved by the individual components alone. In the most preferred embodiments, the result achieved by the combination is more than additive of the results achieved by the individual components alone. In some embodiments, the effective amount of one or both agents used in combination is lower than the effective amount of each agent when administered separately. In some embodiments, the amount of one or both agents when used in the combination therapy is sub-therapeutic when used alone. A treatment regimen of the combination therapy can include one or multiple administrations of the disclosed compounds.

Dosage regimens or cycles of the agents are also provided and can be completely or partially overlapping, or can be sequential.

An effective amount of each of the agents can be administered as a single unit dosage (e.g., as dosage unit), or sub-therapeutic doses that are administered over a finite time interval. Such unit doses may be administered on an hourly or daily basis for a finite time period, such as up to 12 hours, 1 day, 18 hours, 2 days, 3 days, or up to 5 days, etc., are all specifically contemplated.

v. Use as a Sterilizing Agent

The compounds disclosed herein can be used as sterilizing agents, for example in high-risk environments such as in hardware from hospitals or healthcare facilities. The World Health Organization (WHO) estimates that at any time, more than 1.4 million people worldwide are affected by infections acquired in hospitals. Cleaning, disinfection and sterilization saves lives and improves patient outcomes. Between 5% and 10% of patients admitted to modern hospitals in the developed world acquire one or more healthcare-associated infections. The Centers for Disease Control and Prevention (CDC) estimate that approximately 1.7 million healthcare-associated infections occur annually in hospitals in the United States, and are associated with nearly 100,000 deaths each year. Healthcare-associated infections are also an important problem in extended care facilities, including nursing homes and rehabilitation units. Transmission of healthcare-associated pathogens most frequently occurs via the hands of healthcare workers, who inadvertently contaminate their hands during various patient care activities. Less frequently, contaminated surfaces in healthcare facilities may contribute to the spread of healthcare-associated pathogens.

The varying levels of disinfection used in a healthcare facility may be defined by Spaulding's Classification (Sehulster, et al., Guidelines for environmental infection control in health-care facilities. Recommendations from CDC and the Healthcare Infection Control Practices Advisory Committee (HICPAC). Chicago IL; American Society for Healthcare Engineering/American Hospital Association; 2004). Spaulding's levels, non-critical, semi-critical, and critical, are based on the potential for infectious disease spread via equipment, instruments, and furniture as well as the level of sterility normally required for the body part coming in contact with it. Levels of disinfection that correlate with Spaulding's classification are low, intermediate, high, and sterilization. The US Centers for Disease Control (CDC) has further delineated disinfection levels for environmental surfaces in its "Guidelines for Environmental Infection Control in Health-Care Facilities".

Critical items confer a high risk for infection if they are contaminated with any microorganism. Thus, objects that enter sterile tissue or the vascular system must be sterile because any microbial contamination could transmit disease. This category includes surgical instruments, cardiac and urinary catheters, implants, and ultrasound probes used in sterile body cavities. Semicritical items contact mucous membranes or nonintact skin. This category includes respiratory therapy and anesthesia equipment, some endoscopes, laryngoscope blades, esophageal manometry probes, cystoscopes, anorectal manometry catheters, and diaphragm fitting rings. These medical devices should be free from all microorganisms; however, small numbers of bacterial spores are permissible. Specific examples of critical or semi critical instruments include invasive endoscopes such as laparoscopes, and rigid instruments with no operating channel. Arthroscopes and laparoscopes which are inserted into sterile body cavities as well as accessory instrumentation should be sterile. Other examples include gastroscopes, duodenoscopes, sigmoidoscopes, proctoscopes, colonoscopes, bronchoscopes, and laryngoscopes.

D. Kits

Medical kits are also disclosed. The medical kits can include, for example, a dosage supply of disclosed compounds, or a combination thereof, in separately or together in the same admixture. The active agents can be supplied alone (e.g., lyophilized), or in a pharmaceutical composition. The active agents can be in a unit dosage, or in a stock that should be diluted prior to administration. In some embodiments, the kit includes a supply of pharmaceutically acceptable carriers. The kit can also include devices for administration of the active agents or compositions, for example, syringes. In a particular form, the device for administration is an autoinjector. The kits can include printed instructions for administering the compound in a use as described above.

The disclosed compounds, pharmaceutically or agriculturally acceptable salts thereof, compositions, and methods of using can be further understood through the following enumerated paragraphs or embodiments.

1. A composition comprising an extract from a non-leaf portion of *Cassia acutifolia* and an organic solvent or mixture of organic solvents, wherein the organic solvent or mixture of organic solvents comprises a non-naturally occurring organic solvent.

2. The composition of paragraph 1, wherein the non-leaf portion of *Cassia acutifolia* comprises a stem portion.

3. The composition of any of the preceding paragraphs, wherein the extract comprises one or more primary phytochemicals of Casia acutifolio listed in Table 1.

4. The composition of any of the preceding paragraphs, wherein the extract comprises one or more secondary metabolites occurring in Casia acutifolio listed in Table 2.

5. The composition of any of the preceding paragraphs, wherein the mixture of organic solvents comprises an alcohol/non-naturally occurring organic solvent.

6. The composition of any of the preceding paragraphs, wherein the mixture of organic solvents comprises a methanol/non-naturally occurring organic solvent.

7. The composition of any of the preceding paragraphs, wherein the mixture of organic solvents comprises an ethanol/non-naturally occurring organic solvent.

8. The composition of any of the preceding paragraphs, wherein the non-naturally occurring organic solvent comprises dichloromethane or dimethyl sulfoxide.

9. The composition of any of the preceding paragraphs, comprising the extract and (i) dichloromethane or dimethyl sulfoxide, or (ii) a mixture of methanol/dichloromethane or methanol/dimethyl sulfoxide.

10. The composition of any of the preceding paragraphs, having residual amounts of the organic solvent or mixture of organic solvents no more than amounts prescribed by the United States Food and Drug Administration.

11. A pharmaceutical composition comprising an extract from a non-leaf portion of *Cassia acutifolia* and an effective amount of an added pharmaceutically acceptable excipient that preserves the extract.

12. The pharmaceutical composition of paragraph 11, wherein the non-leaf portion of *Cassia acutifolia* comprises a stem portion.

13. The pharmaceutical composition of any of the preceding paragraphs, wherein the extract comprises an alcoholic/non-naturally occurring organic solvent extract of *Cassia acutifolia*.

14. The pharmaceutical composition of any of the preceding paragraphs, wherein the extract comprises an alcoholic/dichloromethane extract of *Cassia acutifolia*.

15. The pharmaceutical composition of any of the preceding paragraphs, wherein the extract comprises one or more primary phytochemicals of Casia acutifolio listed in Table 1.

16. The pharmaceutical composition of any of the preceding paragraphs, wherein the extract comprises one or more secondary metabolites occurring in Casia acutifolio listed in Table 2.

17. The pharmaceutical composition of any of the preceding paragraphs, in the form of tablets, capsules, powders, lozenges, chews, gels, solid solutions, microparticles, nanoparticles, films, sprays, or a combination thereof.

18. The pharmaceutical composition of any of the preceding paragraphs, in the form of an extended-release formulation.

19. A method of treating a subject in need thereof, the method comprising:

administering to the subject an effective amount of the composition of any of the preceding paragraphs or an effective amount of the pharmaceutical composition of any of the preceding paragraphs, wherein the subject has, or is diagnosed as having, a viral infection.

The present invention will be further understood by reference to the following non-limiting examples.

Examples

Example 1: Extracts from *Cassia* Acutifolio Demonstrate Anti-HIV/AID Activities

Method and Materials

*Senna* Makki (Stems) Preparation, Isolation, and Extraction

Dried Saudi *Senna* Makki (stems) was purchased from a herbal shop in Jeddah (source origin: Makkah). The taxonomic identity of plants was confirmed by a local plant taxonomist. Plant stems were pulverized into a fine powder using a mortar, pestle, and grinder. They were then extracted in two stages. First, they were macerated in a mixture of 1.5 mL methanol/dichloromethane (1:1) overnight at room temperature (for about 12 hours). The mixture was vortexed and centrifuged at 14680 rpm for 2 min and crude extracts (i.e., supernatant from this first centrifuged mixture) were collected in a fresh test tube. In the second stage of extraction, 0.4 mL of methanol was added to the remaining marc vortex contents (i.e., the pellets resulting from the centrifuged mixture after the collection of all or some of the supernatant in the first stage). Solvent extraction was allowed to proceed for 30 min at room temperature, before the mixture was centrifugated at 14680 rpm for 2 min. A second extract (i.e., supernatant from this subsequent centrifuged mixture) was then combined with the extract from the previous MeOH/DCM phase (mixture of two extracts together) and stored at −20° C. until required for the experiment.

In sum, in the initial stage of extraction, a crude extract was obtained that encompassed a majority of compounds (e.g., active compounds). The subsequent extraction phase focused on isolating the remaining active compounds from the pellet, aiming to enhance the yield of the crude extract. It is contemplated that the resulting crude extract contains a significant proportion of the compounds present. In another way, during the initial extraction phase, the majority of compounds (e.g., active compounds) were successfully extracted, resulting in a first crude extract derived from a combination of two solvents. The subsequent stage focused on further separating the remaining metabolites that were not extracted in the first phase. This enhancement process was designed to enhance the quality of the crude extract, ultimately yielding a pure crude extract in a mixture of polar solvents.

The following plants or parts of the plants were also investigated and evaluated for potential activity: *Rosa* damascene (leaves); *Salvia officinalis* (stems); *Cassia acutifolia* (leaves); *Thymus vulgaris* (stems); and *Thymus vulgaris* (leaves). All the listed plants or parts were extracted using the same method outlined above.

Estimation of HIV-1 Protease Activity Assay

A quantity of 40 μL diluted recombinant HIV-1 protease (PR) (cat #AS-72028-5; AnaSpec, Fremont, CA, USA) was mixed with 10 μL DMSO solvent of *Senna* Makki (stems) crude extract at a concentration of (100 and 500) μg/mL. The positive controls contained 40 μL diluted HIV-1 protease with 10 μL of 1× assay buffer, the inhibitor controls contained 40 μL diluted HIV-1 protease with 10 μL pepstatin A, the vehicle controls contained 40 μL diluted HIV-1 protease with 10 μL DMSO, and the substrate controls contained 10 μL substrate and 40 μL of 1× assay buffer. In the chemical bioassay, each well was designed to hold a total of 50 μL of reactants. This was subsequently supplemented with 50 μL of enzyme-activating substrate, resulting in a total volume of 100 μL per well. It is noteworthy that each well contained 40 μL of diluted protease. To ensure consistency across the sample quantities, 40 μl of protease was also added to the positive control. Likewise, the last well was deliberately formulated without protease, prompting a recalibration of the quantities under the established protocol.

The reaction mixture was incubated for 15 min at room temperature in dark conditions, then 50 μL HIV-1 PR substrate was added to the mixture to start the reaction and incubated for 60 min at room temperature in dark conditions. Next, a 50 μL stop solution (cat #AS71147) was added to end the reaction. The assay working solutions and controls were freshly prepared utilizing a SensoLyte® 520 HIV-1 protease fluorometric assay kit (#AS-71147, Lot #1028, AnaSpec, Fremont, CA, USA). Reactions were performed in duplicate. The fluorescence intensity of HIV-1 protease efficacy was measured at an emission (Em) wavelength of 528 nm and an excitation (Ex) wavelength of 485 nm per minute using an end-point reading; the following equation calculated the inhibition percentage:

$$RFU = (A_{sample(s)} - A_{substrate})$$

where A is the absorbance. The half-maximal inhibitory concentration (IC50) was estimated from the percentage value.

Gas Chromatography-Mass Spectrometry (GC MS) Analysis

GC-MS analysis was performed using an Agilent (7890B) gas chromatography system together with a 7010B Triple Quad Mass Selective detector and flame ionization. This was operated in full scan mode with the following parameters: speed 2 scans per second, resolving power 1000, mass range from 35 to 700, resolution 0.7 Da, capillary column type DB-5 TR 5 MS 30 m, helium carrier gas, and the oven temperature was programmed at 70° C. Crude extracts were analyzed to detect various constituents of primary metabolites in sample derivatized by drying 10 μL of crude extracts in a Speedvac to evaporate the MeOH solvent, then adding 30 μL of Methoxamine (MOX) derivatization agent to obtain a better separation, and thermomixing at 30° C. for 90 min at 600 rpm. Next, a mixture of 50 μL of N, O-Bis(trimethylsilyl)trifluoroacetamide (BSTFA) and 10 μL of hydrocarbons (c7-c40) Saturated Alkanes Standard 49452-U was added and the samples were vortexed, then thermomixed at 37° C. for 30 min at 600 rpm, before being centrifuged at room temperature for 5 min to ensure removal of particles (purity). Finally, 30 μL was placed into GC-MS brown vials.

UHPLC ID-X Orbitrap Mass Spectrometry Analysis

Untargeted screenings of crude extracts were performed using ultra-high-pressure liquid chromatography (UHPLC) with an Orbitrap ID-X mass spectrometer (UHPLC-Orbitrap ID-X MS). The crude extracts were automatically infused through the UHPLC system using a C18 column (Acquity CSH 100×2.1 mm, 1.7 μm, Agilent Technologies). According to separation, highly resolved chromatography was achieved using a water/acetonitrile gradient. The mobile phase solvents included 100% water with 0.1% formic acid and 100% acetonitrile with 0.1% formic acid. 5 Ml was injected and the flow rate was set to 0.5 mL/min. To develop the experimental workflow and process data, the Xcalibur™ software from Thermo Scientific was utilized. Electrospray ionization in positive mode (ESI+) was applied to the compounds studied and the following parameters were applied: vaporized temperature 100° C., voltage 3500 V, sheath gas 30, auxiliary gas 15, ion source fragmentation 35 V, and capillary temperature 300° C. An intelligent data acquisition workflow (AcquireX) has been implemented to perform an Automated MSn data acquisition of all precursor Ions, and an Automated AcquireX background exclusion list is generated. One MS/MS data was automatically acquired on all full MS features, and one exclusion list was generated for the sample included in the workflow. The Orbitrap ID-X mass spectrometer has been used that contains three mass analyzers. It was used to analyze the m/z of the studies. The Orbitrap IDX spectrometer could reach a high resolution (>120,000) and reliable mass accuracy (<3 ppm mass error). The mass spectrometer was calibrated using a purchasable "Calibration Mix (ESI+) (Thermo Scientific)" by following the manufacturer's guidelines.

Compound Discoverer 3.1 software was used to treat and process data using an untargeted metabolomics workflow which involved identifying different compounds and retention time, detecting unknown compounds across extracted samples, predicting elemental compositions for compounds, hiding chemical background (using blank samples), and identifying compounds using ChemSpider, the MzCloud spectral library (ddMS2) and local compound databases (exact mass or formula).

Results and Discussion

Estimation of HIV-1 Protease Activity Assay

Crude extracts were screened for HIV-1 PR activity. The IC50 values of the crude extract was 2.68 µg/mL. The extract strongly inhibited HIV-1 PR activity when compared to the vehicle control which was approximately (25.1±10.6) µg/mL. The extracts also significantly inhibited HIV-1 PR activity when compared to the pepstatin A which was approximately (28.5±22.4) µg/mL. This activity is related to compounds found in extracts.

Additional plants or their parts were also investigated and evaluated for potential activity: *Rosa* damascene (leaves); *Salvia officinalis* (stems); *Cassia acutifolia* (leaves); *Thymus vulgaris* (stems); and *Thymus vulgaris* (leaves). Each demonstrated a antiviral effect; however, the *Senna* Makki (*Cassia acutifolia*) stems exhibited the most potent inhibitory effect. Furthermore, stem extracts showed higher inhibition compared to the leaves. For instance, *Rosa* damascene (leaves) IC50=7.5 µg/mL; *Salvia officinalis* (stems) IC50=7.8 µg/mL, *Cassia acutifolia* (leaves) IC50=10.7 µg/mL, *Thymus vulgaris* (stems) IC50=5.2 µg/mL, Palestinian *Thymus vulgaris* (leaves) IC50=7.2 µg/mL, Saudi *Thymus vulgaris* (leaves) IC50=12.5 µg/mL, Saudi *Salvia officinalis* (leaves) IC50=5.1 µg/mL, Palestinian *Salvia officinalis* (leaves) IC50=6.8 µg/mL.

Gas Chromatography-Mass Spectrometry (GC MS) Profiling

The results showing peak number, metabolite name, and retention time are set out in Table 1. FIG. 1 shows GC-MS total ion (TIC) of the methanolic/DCM extract chromatograms. Based on the search NIST library and MassHunter software, the GC-MS analysis revealed 49 metabolites. As observed from the spectra, Fructopyranose and Pinitol compounds exhibited higher intensities at 26.2 and 26.4 RT, respectively. The xylose 4TMS natural product at 22.01 RT is a pentose monosaccharide with an aldehyde group and a late metabolite of L-ascorbate, Xylose is an element that binds glycosaminoglycans (GAGs) to core proteins and has only one binding site (Vitro & Cheudjeu, 2023). D-xylose in the biosynthesis of heparan sulfate (HS), chondroitin sulfate (CS), dermatan sulfate (DS), and heparin (Hep) indicate that quantities of D-xylose in an organism directly affect GAGs amount in organism (Cheudjeu, 2020). D-xylose has been shown to significantly stimulate the synthesis and secretion of PGs and GAGs on the surface of epidermis cells such as fibroblasts and keratinocytes (WO1999024009A1; Dumas, MarcUses of d-xylose & Bonte, 2002). According to Cheudjeu's, D-xylose showed antiviral impacts against HIV-1 with an IC50 124.4 mM (Vitro & Cheudjeu, 2023). In a study utilizing Molecular Docking, nucleosides derived from fructopyranose were considered promising to inhibit RT/AIDS enzyme. The analysis of the MolDock Score indicated that 22 of the nucleoside analogs performed better than drugs Emtricitabine and Stavudine. Additionally, 15 compounds out of the total 22 had better results than Telbivudine, and 13 outperformed didanosine. Interestingly, one specific compound from the study had a better result than 10 (out of 12) bioactive drugs that are commonly used in anti-HIV drugs (Monteiro, Scotti, & Scotti, 2019). Pinitol was found in significant levels in Sutherlandia plant, this compound is thought to treat wasting seen in AIDS patients (Ostlund & Sherman, 1998). A previous study demonstrated that Palmitic Acid (PA) can block HIV-1 entry and infection by directly inhibiting gp120-CD4+ complex binding in host cells. This inhibition occurs in a dose-dependent manner (Lee et al., 2009). Another study confirms the efficacy of saturated fatty acids palmitic acid, Oleic acid, and Linoleic acid, extracted from *Auricularia polytricha*, against protease with an IC50 0.80±0.08 mg/ml (Sillapachaiyaporn, Nilkhet, Ung, & Chuchawankul, 2019).

UHPLC ID-X Orbitrap Mass Spectrometry Profiling

Figure 2:
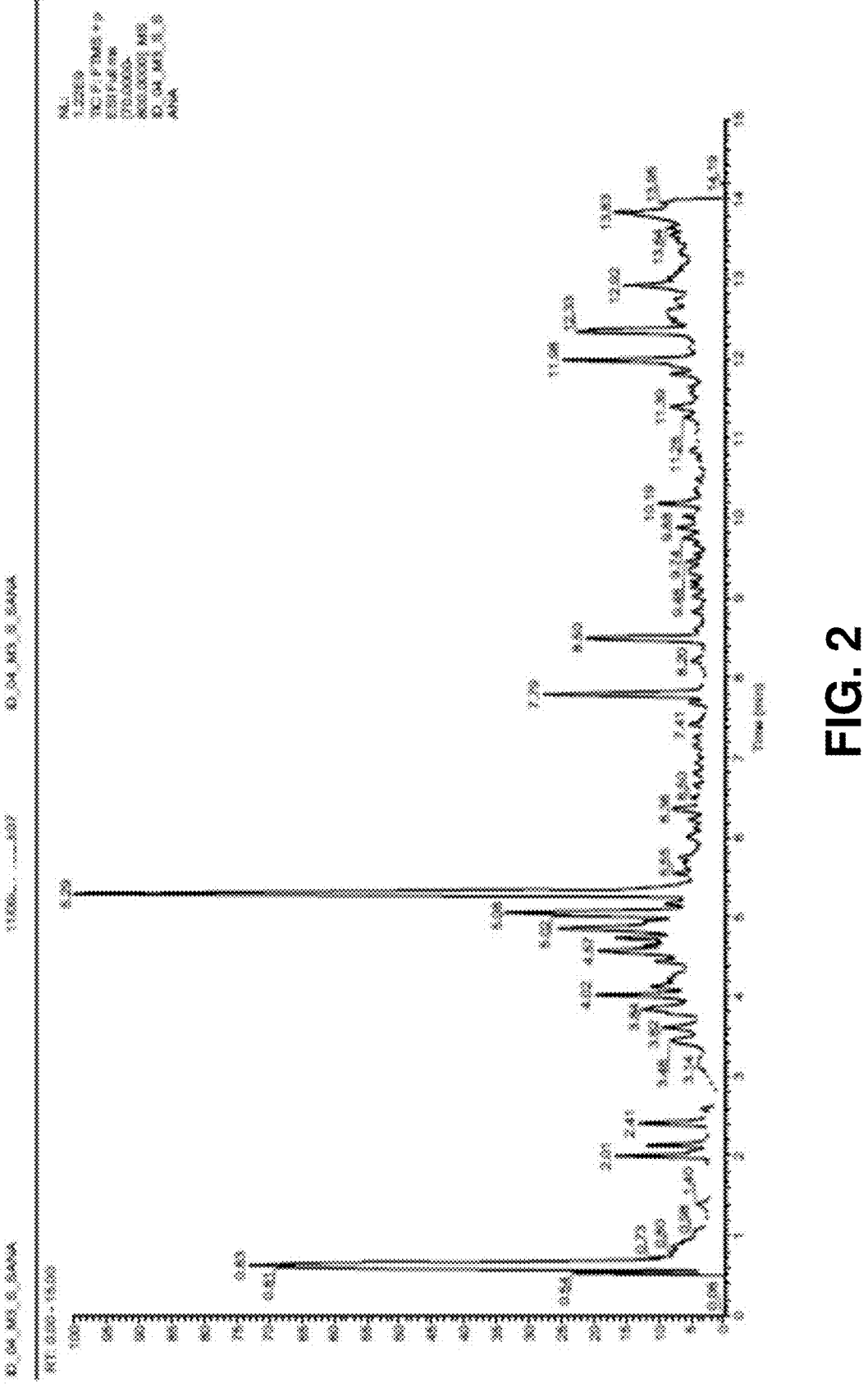
FIG. 2 is an ESI chromatogram of *Cassia acutifolia* with LC-MS in positive ion mode.

Liquid chromatography-mass spectrometry (LC-MS) is used to conduct analyses of diverse secondary metabolites (polar/nonpolar, acidic/basic, etc.) with various physical and chemical properties in a stationary phase. Column C18 to LC-MS instrumentation was applied to achieve outstanding efficiency in the fractionation and determination of semipolar compounds. UHPLC analysis results for methanolic/DCM extract obtained from *Senna* Makki are shown in Table 2 and FIG. 2 which identifies compounds and sets out the retention times, formulas, and molecular ion [M+H]. Extract profiling revealed 17 secondary metabolites. As observed from the spectra aloesin at 5.29 RT showed the higher intensity compound. Previous studies showed that a variety of furanone derivatives had a positive impact on preventing viral replication of influenza HPAI-H5N1 (AIV), gastroenteric viruses rotavirus, and adenovirus (Youssef et al., 2023) (El-Shanbaky, Abd El-Hameed, & Mohamed, 2020). Phloroglucinol derivatives from *Hypericum scruglii* inhibited HIV-1 reverse transcriptase and integrase in biochemical assays with IC50 values ranging from 4.1-25.5 µM and 7.3-13 µM respectively (Sanna et al., 2018). The bicyclic molecule indole has gained attention due to its various pharmacological potencies and several studies have designed antiviral drugs containing indole to combat viral infections (Dorababu, 2020); Indole-2-carboxylic acid was developed as a potent scaffold for inhibiting the strand transfer activity of HIV-1 integrase, the derivative was found to effectively inhibit integrase activity by binding to the two Mg2+ ions present within the enzyme's active site. The indole core and $C_2$ carboxyl group of the derivative chelated Mg2+ ions then blocked the enzyme's catalytic activity with an IC50 0.13 µM (Wang et al., 2023). While saponaroxin derived from the fungus *Arthrinium* sp. found in mangrove sediment has demonstrated significant anti-HIV activity (Yang et al., 2023). Isorhamnetin, extracted from *Carica papaya* leaves, possesses drug-like properties, and showed a potent impact against SARS-Coronavirus. In a previous study, isorhamnetin, an anti-HBV flavonol was identified through HPLC analysis. At a concentration of 10 µg/mL it reduced HBsAg levels by approximately 30.5% (Akhtar et al., 2023) (Parvez, Al-Dosari, Basudan, & Herqash, 2022). Aloesin isolated from root extracts of methanolic *R. nepal-*

*ensis* showed pharmacological activities including antimicrobial, antioxidant, antitumor, antidiabetic, and anti-inflammatory properties (Gonfa, Beshah, Tadesse, Bachheti, & Bachheti, 2021). Aloesin isolated from Aloe vera was also found to possess skin wound healing properties (Wahedi et al., 2017) (Fouché, Willers, Hamman, Malherbe, & Steenekamp, 2020).

TABLE 1

Primary phytochemicals in *Cassia acutifolia* were identified using GC-MS.

| Peak NO. | Identification | RT |
|---|---|---|
| 1 | L-Alanine, 2TMS | 11.1 |
| 2 | L-Valine, 2TMS | 14.05 |
| 3 | Ethanolamine, 3TMS | 5.2 |
| 4 | Glycerol, 3TMS | 15.3 |
| 5 | L-Isoleucine, 2TMS | 15.9 |
| 6 | L-Proline, 2TMS | 16.1 |
| 7 | Butanedioic acid, 2TMS | 16.6 |
| 8 | Glyceric acid, 3TMS | 16.7 |
| 9 | Pipecolic acid, 2TMS | 17.7 |
| 10 | L-Threonine, 3TMS | 18.0 |
| 11 | 4-Ketoglucose, methoxime, trimethylsilyl | 19.7 |
| 12 | Malic acid, 3TMS | 20.3 |
| 13 | Ribitol, 5TMS | 20.4 |
| 14 | 4-Aminobutanoic acid, 3TMS | 21.2 |
| 15 | 2,3-Dihydroxy-2-methylpropanoic acid, 3TMS | 21.3 |
| 16 | D-(−)-Erythrose, tris(trimethylsilyl) ether, trimethylsilyloxime (isomer 1) | 21.3 |
| 17 | Erythronic acid, tetrakis(trimethylsilyl) | 21.6 |
| 18 | Xylose, 4TMS | 22.08 |
| 19 | Posiple [L-Proline, 2TMS] | 22.5 |
| 20 | D-Arabinose, tetrakis(trimethylsilyl) ether, methyloxime (syn) | 23.5 |
| 21 | D-(−)-Lyxose, tetrakis(trimethylsilyl) ether, methyloxime (anti) | 23.7 |
| 22 | Ribitol, 5TMS [Isomer] | 24.06 |
| 23 | D-(−)-Rhamnose, tetrakis(trimethylsilyl) ether, methyloxime (syn) | 24.5 |
| 24 | D-(+)-Ribono-1,4-lactone, 3TMS | 25.2 |
| 25 | D-Allofuranose, pentakis(trimethylsilyl) ether | 25.6 |
| 26 | D-(−)-Tagatofuranose, pentakis(trimethylsilyl) ether (isomer 1) | 26.0 |
| 27 | D-(−)-Fructopyranose, 5TMS | 26.2 |
| 28 | D-Pinitol, pentakis(trimethylsilyl) ether | 26.4 |
| 29 | D-(−)-Fructose, pentakis(trimethylsilyl) ether, methyloxime (anti) | 27.1 |
| 30 | D-(−)-Fructose, pentakis(trimethylsilyl) ether, methyloxime (syn) | 27.3 |
| 31 | d-Galactose, 2,3,4,5,6-pentakis-O-(trimethylsilyl)-, o-methyloxyme, (1E)- | 27.5 |
| 32 | d-Glucose, 2,3,4,5,6-pentakis-O-(trimethylsilyl)-, o-methyloxyme, (1Z)- | 27.6 |
| 33 | d-Mannose, 2,3,4,5,6-pentakis-O-(trimethylsilyl)-, o-methyloxyme, (1E)- | 27.9 |
| 34 | D-Chiro-Inositol, 6TMS | 28.5 |
| 35 | D-Pinitol, pentakis(trimethylsilyl) ether | 28.6 |
| 36 | β-D-(+)-Mannopyranose, 5TMS | 29.08 |
| 37 | D-Pinitol, pentakis(trimethylsilyl) ether(Isomer) | 29.3 |
| 38 | Palmitic Acid, TMS | 30.6 |
| 39 | D-Chiro-Inositol, 6TMS[Isomer] | 30.7 |
| 40 | Linoleic acid, TMS | 33.1 |
| 41 | α-Linolenic acid, TMS | 33.2 |
| 43 | Sucrose, 8TMS | 38.07 |
| 44 | Aucubin, hexakis(trimethylsilyl) ether | 38.6 |
| 45 | Methyl galactoside, 4TMS | 39.5 |
| 46 | Lactose, 8TMS | 40.09 |
| 47 | D-(+)-Cellobiose, octakis(trimethylsilyl) ether, methyloxime (isomer 2) | 40.4 |
| 48 | D-(+)-Turanose, octakis(trimethylsilyl) ether | 44.2 |
| 49 | Oleic acid, eicosyl ester | 44.4 |

No. = peak number,
RT = retention time.

TABLE 2

Secondary metabolites identified in methanolic/DCM extract of *Cassia acutifolia*.

| PEAK NO. | Identification | Formula | RT | [M + H] Mass |
|---|---|---|---|---|
| 1 | N-Propyloctadecan-amide | C21 H43 NO | 0.54 | 326.34174 |
| 2 | 2(5H)-Furanone | C4 H4 O2 | 0.64 | 85.02828 |
| 3 | Phloroglucinol | C6 H6 O3 | 0.64 | 127.0388 |
| 4 | 3-Vinylaniline | C8 H9 N | 1.39 | 120.08065 |
| 5 | Pantothenic acid (VitaminB5) | C9 H17 N O5 | 1.99 | 220.118 |
| 6 | 4-Indolecarbaldehyde | C9 H7 N O | 2.01 | 146.06003 |
| 7 | Resorcinol | C6 H6 O2 | 2.41 | 111.04386 |
| 8 | Rhamnosyllactone A | C20 H26 O11 | 3.62 | 443.15414 |
| 9 | Saponaroxin C | C19 H24 O9 | 3.83 | 397.14886 |
| 10 | Sinapinic acid | C11 H12 O5 | 4.02 | 207.06514 |
| 11 | Isorhamnetin | C16 H12 O7 | 5.02 | 317.06534 |
| 12 | Aloesin | C19 H22 O9 | 5.29 | 377.12292 |
| 13 | Diosmetin | C16 H12 O6 | 6.36 | 301.07083 |
| 14 | Styrene | C8 H8 | 7.79 | 105.06976 |
| 15 | 1, 4, 7, 8, 11, 14, 17, 20, 21, 24, 29, 32, 33, 36-Tetradecaaza-pentacyclo [12.12.12.1~6, 9~.1~19, 22~.1~31, 34~] hentetraconta-6(41), 8, 19, 22(40), 31(39), 33-hexaene | C27 H48 N14 | 11.98 | 569.42523 |
| 16 | DELTA 15 CIS MONONERVONIN | C27 H52 O4 | 12.92 | 441.39328 |
| 17 | Stigmasterol | C29 H48 O | 13.82 | 413.37747 |

No. = number of peaks,
RT = retention time, [M + H]+
(m/z) = positive mass ion of H.

CONCLUSION

*Cassia acutifolia* is an effectual medicinal plant due to its pharmaceutically active phytochemicals, including primary and secondary metabolites. Polar Stems crude extract showed greater antiretroviral activity against HIV-1 protease with IC50 2.68 µg/mL, compared to control. This influence is attributed to bioactive components in *Senna* makki stems, which contributed to activity against HIV-1 and other viruses. Our findings provide promising and novel data for drug discovery and development against HIV/AIDS.

REFERENCES

Abdellatif, N., Abdelhameed, R., Eltamany, E., & Badr, J. (2023). Review on Phytochemical Constituents of Plants of Genus *Cassia*. Records of Pharmaceutical and Biomedical Sciences, 7(2), 93-110. https://doi.org/10.21608/rpbs.2023.198575.1215

Akhtar, N., Husen, A., Dwibedi, V., & Rath, S. K. (2023). Promising Antiviral Herbal and Medicinal Plants. Promising Antiviral Herbal and Medicinal Plants. Boca Raton: CRC Press. https://doi.org/10.1201/9781003329169

Cheudjeu, A. (2020). Correlation of D-xylose with severity and morbidity-related factors of COVID-19 and possible therapeutic use of D-xylose and antibiotics for COVID-19. Life Sciences, 260 (August), 118335. https://doi.org/10.1016/j.lfs.2020.118335

DEBOUCK, C. (1992). The HIV-1 Protease as a Therapeutic Target for AIDS. AIDS Research and Human Retroviruses, 8(2), 153-164. https://doi.org/10.1089/aid.1992.8.153

Dorababu, A. (2020). Indole—a promising pharmacophore in recent antiviral drug discovery. RSC Medicinal Chemistry, 11(12), 1335-1353. https://doi.org/10.1039/DOMD00288G Dumas, MarcUses of d-xylose, the esters thereof and oligosaccharides containing xylose for improving the functionality of epidermal cells, & Bonte, F. (2002). Uses of d-xylose, the esters thereof and oligosaccharides containing xylose for improving the functionality of epidermal cells. https://doi.org/https://patentimages.storage.googleapis.com/c6/1f/e0/bd12dd8e8b 8624/WO1999024009A1.pdf El-Shanbaky, H., Abd El-Hameed, R., & Mohamed, M. (2020). Synthesis of Heterocyclic and Non-heterocyclic Compounds Derived from Novel 2-Furanones and Evaluation of their Anti-viral Activity. Journal of Advanced Pharmacy Research, 0(0), 0-0. https://doi.org/10.21608/aprh.2020.49788.1120

Fouché, M., Willers, C., Hamman, S., Malherbe, C., & Steenekamp, J. (2020). Wound Healing Effects of Aloe muth-muth: In Vitro Investigations Using Immortalized Human Keratinocytes (HaCaT). Biology, 9(11), 350. https://doi.org/10.3390/biology9110350

Gonfa, Y. H., Beshah, F., Tadesse, M. G., Bachheti, A., & Bachheti, R. K. (2021). Phytochemical investigation and potential pharmacologically active compounds of Rumex nepalensis: an appraisal. Beni-Suef University Journal of Basic and Applied Sciences, 10(1), 1-11. https://doi.org/10.1186/s43088-021-00110-1

Hajjar, D., Kremb, S., Sioud, S., Emwas, A.-H., Voolstra, C. R., & Ravasi, T. (2017). Anti-cancer agents in Saudi Arabian herbals revealed by automated high-content imaging. PLOS ONE, 12(6), e0177316. https://doi.org/10.1371/journal.pone.0177316

Laila, U., Akram, M., Shariati, M. A., Hashmi, A. M., Akhtar, N., Tahir, I. M., . . . . Ahmad, S. (2019). Role of medicinal plants in HIV/AIDS therapy. Clinical and Experimental Pharmacology and Physiology, 46(12), 1063-1073. https://doi.org/10.1111/1440-1681.13151

Lee, D. Y.-W., Lin, X., Paskaleva, E. E., Liu, Y., Puttamadappa, S. S., Thornber, C., . . . Canki, M. (2009). Palmitic Acid Is a Novel CD4 Fusion Inhibitor That Blocks HIV Entry and Infection. AIDS Research and Human Retroviruses, 25(12), 1231-1241. https://doi.org/10.1089/aid.2009.0019

Leteane, M. M., Ngwenya, B. N., Muzila, M., Namushe, A., Mwinga, J., Musonda, R., Andrae-Marobela, K. (2012). Old plants newly discovered: Cassia sieberiana D. C. and Cassia abbreviata Oliv. Oliv. root extracts inhibit in vitro HIV-1c replication in peripheral blood mononuclear cells (PBMCs) by different modes of action. Journal of Ethnopharmacology, 141(1), 48-56. https://doi.org/10.1016/j.jep.2012.01.044

Monteiro, A., Scotti, M., & Scotti, L. (2019). MOLECULAR DOCKING OF FRUCTOSE-DERIVED NUCLEOSIDE ANALOGS AGAINST REVERSE TRANSCRIPTASE OF HIV-1. In Proceedings of MOL2NET 2019, International Conference on Multidisciplinary Sciences, 5th edition (p. 6178). Basel, Switzerland: MDPI. https://doi.org/10.3390/mol2net-05-06178

Omoruyi, B. E., Ighodaro, D. I., Afolayan, A. J., & Bradley, G. (2020). Inhibition of HIV-1 Protease by Carpobrotus edulis (L.). Evidence-Based Complementary and Alternative Medicine, 2020, 1-14. https://doi.org/10.1155/2020/9648056 Ostlund, R. E., & Sherman, R. (1998). PINITOL AND DERIVATIVES THEREOF FOR THE TREATMENT OF METABOLIC DISORDERS.

Parvez, M. K., Al-Dosari, M. S., Basudan, O. A., & Herqash, R. N. (2022). The anti-hepatitis B virus activity of sea buckthorn is attributed to quercetin, kaempferol and isorhamnetin. Biomedical Reports, 17(5). https://doi.org/10.3892/br.2022.1573

Popović-Djordjević, J., Quispe, C., Giordo, R., Kostić, A., Katanić Stanković, J. S., Tsouh Fokou, P. V., . . . . Calina, D. (2022). Natural products and synthetic analogues against HIV: A perspective to develop new potential anti-HIV drugs. European Journal of Medicinal Chemistry, 233. https://doi.org/10.1016/j.ejmech.2022.114217

Sanna, C., Scognamiglio, M., Fiorentino, A., Corona, A., Graziani, V., Caredda, A., . . . . Esposito, F. (2018). Prenylated phloroglucinols from Hypericum scruglii, an endemic species of Sardinia (Italy), as new dual HIV-1 inhibitors effective on HIV-1 replication. PLOS ONE, 13(3), 1-19. https://doi.org/10.1371/journal.pone.0195168

Sillapachaiyaporn, C., Nilkhet, S., Ung, A. T., & Chuchawankul, S. (2019). Anti-HIV-1 protease activity of the crude extracts and isolated compounds from Auricularia polytricha. BMC Complementary and Alternative Medicine, 19(1), 1-10. https://doi.org/10.1186/s12906-019-2766-3

Vitro, H.-N.-I., & Cheudjeu, A. (2023). D-Xylose, a Stimulator of Heparan Sulfate Biosynthesis, Exhibits Antiviral Properties Against SARS-COV-2, ZIKV, HCMV and HIV-1 NL4-3 In Vitro, 1-28.

Wahedi, H. M., Jeong, M., Chae, J. K., Do, S. G., Yoon, H., & Kim, S. Y. (2017). Aloesin from Aloe vera accelerates skin wound healing by modulating MAPK/Rho and Smad signaling pathways in vitro and in vivo. Phytomedicine, 28, 19-26. https://doi.org/10.1016/j.phymed.2017.02.005

Wang, Y. C., Zhang, W. L., Zhang, R. H., Liu, C. H., Zhao, Y. L., Yan, G. Y., . . . . Zhou, M. (2023). The Discovery of Indole-2-carboxylic Acid Derivatives as Novel HIV-1 Integrase Strand Transfer Inhibitors. Molecules, 28(24). https://doi.org/10.3390/molecules28248020

Yang, B., Li, C., Chen, Y., He, Y., She, J., Zhou, X., . . . . Peng, B. (2023). Arthproliferins A-D, Four New Sesterterpenes from the Mangrove-Sediment-Derived Fungus Arthrinium sp. SCSIO41221. Molecules, 28(21). https://doi.org/10.3390/molecules28217246

Youssef, Y. M., Azab, M. E., Elsayed, G. A., El-Sayed, A. A., Hassaballah, A. I., El-Safty, M. M., . . . . El-Helw, E. A. E. (2023). Synthesis and antioxidant, antimicrobial, and antiviral activity of some pyrazole-based heterocycles using a 2(3H)-furanone derivative. Journal of the Iranian Chemical Society, 20(9), 2203-2216. https://doi.org/10.1007/s13738-023-02814-w.

We claim:

1. A composition comprising an extract from a non-leaf portion of Cassia acutifolia and an organic solvent or mixture of organic solvents, wherein the organic solvent or mixture of organic solvents comprises a non-naturally occurring organic solvent and wherein the non-naturally occurring solvent is a solvent comprising one or more of dichloromethane, dimethyl sulfoxide, propylene glycol, poly(ethylene glycol), ethyl acetate, benzyl alcohol, glycerol, ethanol, dimethyl formamide, and/or acetone; and wherein the extract from said non-leaf portion of Cassia acutifolia increases inhibition of viral proteases in a subject as compared to administration of an extract from a leaf portion of *Cassia acutifolia*.

2. The composition of claim 1, wherein the non-leaf portion of *Cassia acutifolia* comprises a stem portion.

3. The composition of claim 1, wherein the extract comprises one or more primary phytochemicals of *Cassia acutifolia* selected from the group consisting of L-alanine, L-valine, ethanolamine, glycerol, L-isoleucine, L-proline, butanedioic acid, glyceric acid, pipecolic acid, L-threonine, 4-ketoglucose, malic acid, ribitol, 4-aminobutanoic acid, 2,3-dihydroxy-2-methylpropanoic acid, D-(–)-erythrose, erythronic acid, xylose, L-proline, D-arabinose, D-(–)-lyxose, ribitol, D-(–)-rhamnose, D-(+)-ribono-1,4-lactonc, D-allofuranose, D-(–)-tagatofuranose, D-(–)-fructopyranose, D-pinitol, D-(–)-fructose, D-(–)-fructose, D-galactose, D-glucose, D-mannose, D-chiro-inositol, β-D-(+)-mannopyranose, palmitic acid, linoleic acid, α-linolenic acid, sucrose, aucubin, methyl galactoside, lactose, D-(+)-cellobiose, D-(+)-turanose, and oleic acid.

4. The composition of claim 1, wherein the extract comprises one or more secondary metabolites occurring in *Cassia acutifolia* selected from the group consisting of N-propyloctadecanamide, 2(5H)-furanone, phloroglucinol, 3-vinylaniline, pantothenic acid, 4-indolecarbaldehyde, resorcinol, rhamnosyllactone A, saponaroxin C, sinapinic acid, isorhamnetin, aloesin, diosmetin, styrene, delta-15-cis-mononervonin, and stigmasterol.

5. The composition of claim 1, wherein the mixture of organic solvents comprises an alcohol/non-naturally occurring organic solvent mixture.

6. The composition of claim 1, wherein the mixture of organic solvents comprises a methanol/non-naturally occurring organic solvent mixture.

7. The composition of claim 1, wherein the mixture of organic solvents comprises an ethanol/non-naturally occurring organic solvent mixture.

8. The composition of claim 1, wherein the non-naturally occurring organic solvent comprises dichloromethane or dimethyl sulfoxide.

9. A composition of claim 1, comprising said extract from a non-leaf portion of *Cassia acutifolia* and (i) dichloromethane or dimethyl sulfoxide, or (ii) a mixture of methanol/dichloromethane or methanol/dimethyl sulfoxide.

10. A pharmaceutical composition comprising:
(i) an extract from a non-leaf portion of *Cassia acutifolia* according to claim 1 or obtained therefrom, wherein the extract from said non-leaf portion of *Cassia acutifolia* is present in an amount sufficient to increase inhibition of viral proteases in a subject as compared to administration of an extract from a leaf portion of *Cassia acutifolia*; and
(ii) an effective amount of an added pharmaceutically-acceptable excipient that preserves the extract.

11. The pharmaceutical composition of claim 10, wherein the non-leaf portion of *Cassia acutifolia* comprises a stem portion.

12. The pharmaceutical composition of claim 10, wherein the extract comprises an alcoholic/non-naturally occurring organic solvent extract of *Cassia acutifolia*, and wherein the non-naturally occurring solvent is a solvent comprising one or more of dichloromethane, dimethyl sulfoxide, propylene glycol, poly(ethylene glycol), ethyl acetate, benzyl alcohol, glycerol, ethanol, dimethyl formamide, and/or acetone.

13. The pharmaceutical composition of claim 10, wherein the extract comprises an alcoholic/dichloromethane extract of *Cassia acutifolia*.

14. The pharmaceutical composition of claim 10, wherein the extract comprises one or more primary phytochemicals of *Cassia acutifolia* selected from the group consisting of L-alanine, L-valine, ethanolamine, glycerol, L-isoleucine, L-proline, butanedioic acid, glyceric acid, pipecolic acid, L-threonine, 4-ketoglucose, malic acid, ribitol, 4-aminobutanoic acid, 2,3-dihydroxy-2-methylpropanoic acid, D-(–)-erythrose, erythronic acid, xylose, L-proline, D-arabinose, D-(–)-lyxose, D-(–)-rhamnose, D-(+)-ribono-1,4-lactonc, D-allofuranose, D-(–)-tagatofuranose, D-(–)-fructopyranose, D-pinitol, D-(–)-fructose, D-galactose, D-glucose, D-mannose, D-chiro-inositol, β-D-(+)-mannopyranose, palmitic acid, linoleic acid, α-linolenic acid, sucrose, aucubin, methyl galactoside, lactose, D-(+)-cellobiose, D-(+)-turanose, and oleic acid.

15. The pharmaceutical composition of claim 10, wherein the extract comprises one or more secondary metabolites occurring in *Cassia acutifolia* selected from the group consisting of N-propyloctadecanamide, 2(5H)-furanone, phloroglucinol, 3-vinylaniline, pantothenic acid (vitamin B5), 4-indolecarbaldehyde, resorcinol, rhamnosyllactone a, saponaroxin c, sinapinic acid, isorhamnetin, aloesin, diosmetin, styrene, delta-15-cis-mononervonin, and stigmasterol.

16. The pharmaceutical composition of claim 10, where the composition is in the form of tablets, capsules, powders, lozenges, chews, gels, solid solutions, microparticles, nanoparticles, films, sprays, or a combination thereof.

17. The pharmaceutical composition of claim 10, where the composition is in the form of an extended-release formulation.

18. A method of treating a subject in need thereof, the method comprising:
administering to the subject an effective amount of the composition of claim 1, wherein the subject has, or is diagnosed as having, a viral infection.

19. A method of treating a subject in need thereof, the method comprising:
administering to the subject an effective amount of the pharmaceutical composition of claim 10, wherein the subject has, or is diagnosed as having, a viral infection.

20. A composition comprising:
(i) an extract of *Cassia acutifolia* obtained from a non-leaf portion of the *Cassia acutifolia* by solid-liquid extraction, wherein the extract from said non-leaf portion of *Cassia acutifolia* is present in an effective amount to increases inhibition of viral proteases in a subject as compared to administration of an extract from a leaf portion of *Cassia acutifolia*; and
(ii) an organic solvent or mixture of organic solvents,
wherein the organic solvent or mixture of organic solvents is used to perform the extraction,
wherein the organic solvent is dichloromethane or dimethyl sulfoxide, and
wherein the mixture of organic solvents is methanol/dichloromethane or methanol/dimethyl sulfoxide.

* * * * *